United States Patent
Miller et al.

(10) Patent No.: US 11,400,079 B2
(45) Date of Patent: Aug. 2, 2022

(54) ANTIBACTERIAL MONOBACTAMS

(71) Applicant: University of Notre Dame du Lac, South Bend, IN (US)

(72) Inventors: Marvin J. Miller, South Bend, IN (US); Serena Carosso, South Bend, IN (US); Rui Liu, South Bend, IN (US); Patricia Miller, South Bend, IN (US)

(73) Assignee: University of Notre Dame du Lac, South Bend, IN (US)

( * ) Notice: Subject to any disclaimer, the term of this patent is extended or adjusted under 35 U.S.C. 154(b) by 208 days.

(21) Appl. No.: 16/753,243

(22) PCT Filed: Oct. 2, 2018

(86) PCT No.: PCT/US2018/053917
§ 371 (c)(1),
(2) Date: Apr. 2, 2020

(87) PCT Pub. No.: WO2019/070672
PCT Pub. Date: Apr. 11, 2019

(65) Prior Publication Data
US 2020/0330438 A1 Oct. 22, 2020

Related U.S. Application Data

(60) Provisional application No. 62/568,578, filed on Oct. 5, 2017.

(51) Int. Cl.
| | |
|---|---|
| A61K 31/427 | (2006.01) |
| A61P 31/04 | (2006.01) |
| A61K 31/431 | (2006.01) |
| A61K 38/12 | (2006.01) |

(52) U.S. Cl.
CPC ............ *A61K 31/427* (2013.01); *A61P 31/04* (2018.01); *A61K 31/431* (2013.01); *A61K 38/12* (2013.01)

(58) Field of Classification Search
CPC .... A61K 31/427; A61K 31/431; A61K 38/12; A61P 31/04
USPC .................................................... 514/210.15
See application file for complete search history.

(56) References Cited

U.S. PATENT DOCUMENTS

| | | |
|---|---|---|
| 4,565,654 A | 1/1986 | Miller |
| 4,992,544 A | 2/1991 | Miller |
| 5,250,676 A | 10/1993 | Gasparski et al. |
| 9,862,680 B2 * | 1/2018 | Miller .................. C07D 205/08 |
| 2017/0355671 A1 | 12/2017 | Miller et al. |

OTHER PUBLICATIONS

Bellettini et al., "Intermolecular Addition of Amines to an N-Tosyloxy beta-Lactam(1)," J Org Chem., 61 (22):7959-7962, Nov. 1996.
Bulychev et al., "N-Sulfonyloxy-(l-lactam Inhibitors for (l-Lactamases," Tetrahedron, 56:5719-5728, Feb. 2000.
Bulychev et al., "Potent Mechanism-based Inhibition of the TEM-1 .beta.-lactamase by Novel N-Sulfonyloxy .beta.-lactams," J. Am. Chem. Soc., 117(22):5938-5943, Jun. 1995.
Fischbach et al., "Antibiotics for Emerging Pathogens," Science, 325(5944):1089-1093, Aug. 2009.
Fisher et al., "Bacterial Resistance to Beta-lactam Antibiotics: Compelling Opportunism, Compelling Opportunity," Chem Rev., 105(2):395-424, Feb. 2005.
Horne et al., "Heterocyclic Peptide Backbone Modifications in an Alpha-helical Coiled Coil," J Am Chem Soc., 126 (47): 15366-15367, Dec. 2004.
International Search Report and Written Opinion of the ISA/US dated Dec. 6, 2018 in International Application No. PCT/US2018/053917; 6pgs.
Kotra et al., "β-Lactam Antibiotics, β-lactamases and Bacterial Resistance," Bulletin de l'Institut Pasteur, 96 (3):139-150, Jul.-Sep. 1998.
Rajendra et al., "Intramolecular Electrophilic Additions to Olefins in Organic Syntheses. Stereoselective Synthesis of 3,4-substituted .beta.-lactams by Bromine-induced Oxidative Cyclization of O-acyl .beta.,.gamma.-unsaturated Hydroxamic Acid Derivatives," J. Org. Chem., 52(20):4471-4477, Oct. 1987.
Teng et al., "Diastereoselective Addition of Nucleophiles to the C3 position of N-(tosyloxy)-.beta.-lactams," J. Am. Chem. Soc., 115(2):548-554, Jan. 1993.
Teng et al., "β-Lactamase Inhibitors Derived from N-tosyloxy-β-lactams," Bioorg Med Chem., 1(2):151-154, Aug. 1993.

* cited by examiner

*Primary Examiner* — Kristin A Vajda
(74) *Attorney, Agent, or Firm* — Haukaas Fortius PLLC; Michael H. Haukaas

(57) ABSTRACT

Bromine induced lactamization of vinyl acetohydroxamates facilitated syntheses of monocyclic β-lactams suitable for incorporation of a thiomethyl and extended functionality at the C(4) position. Elaboration of the resulting substituted N-hydroxy-2-azetidinones allowed incorporation of functionalized α-amino substituents appropriate for enhancement of antibiotic activity. Evaluation of antibacterial activity against a panel of Gram-positive and Gram-negative bacteria revealed structure-activity-relationships (SAR) and identification of potent new monobactam antibiotics. The corresponding bis-catechol conjugate, 42, has excellent activity against Gram-negative bacteria including carbapenemase and carbacephalosporinase producing strains of *Acinetobacter baumannii* which have been listed by the WHO as being of critical concern worldwide.

21 Claims, No Drawings

ANTIBACTERIAL MONOBACTAMS

RELATED APPLICATIONS

This application is a National Stage filing under 35 U.S.C. § 371 of International Application No. PCT/US2018/053917 filed Oct. 2, 2018, which claims priority under 35 U.S.C. § 119(e) to U.S. Provisional Patent Application No. 62/568,578, filed Oct. 5, 2017, which applications are incorporated herein by reference.

GOVERNMENT SUPPORT

This invention was made with government support under Grant No. 5R21AI098689 awarded by the National Institutes of Health. The government has certain rights in the invention.

BACKGROUND OF THE INVENTION

The clinical introduction of penicillin in the 1940s is a milestone in the history of mankind since it led to a drastic decrease of the mortality rate caused by bacterial infections and also to an unprecedented improvement in the quality of life. The two decades between 1940 and 1960 have been defined as the "golden era of antibiotics" in which several new classes of antibiotics were developed and introduced on the market. However, infectious diseases have not been eradicated since bacteria progressively developed a wide variety of mechanisms to survive exposure to antibiotics, giving rise to the growing phenomenon of bacterial resistance. As a consequence, the commonly used antibiotics are becoming less and less effective and the need for new antibiotics, with novel structures and/or mechanism of action, has become more pressing.

Scheme A. N-Sulfonated monocyclic β-lactams.

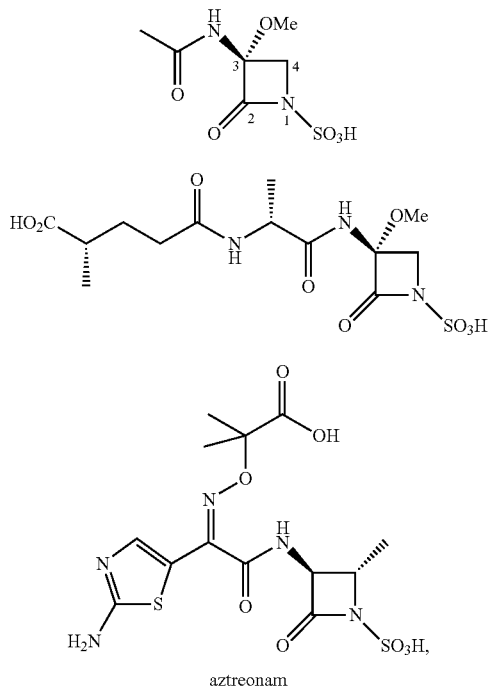

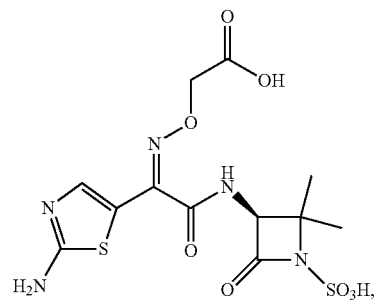
tigemonam

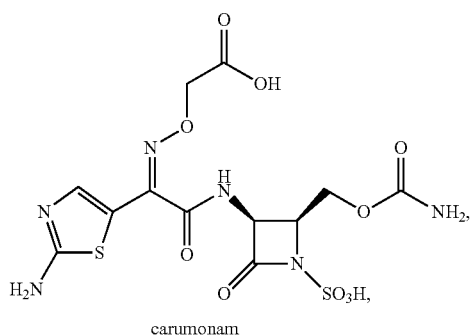
carumonam

Monocyclic, N-sulfonated β-lactams are a family of antibiotic compounds produced by bacteria that was discovered by the Squibb and Takeda groups in 1981. These compounds are produced by a variety of Gram-negative bacteria and are characterized by a 2-oxoazetidine-1-sulfonic acid moiety. Their discovery represented an important advance in the fight against infectious diseases and bacterial resistance to antibiotics since demonstration that monocyclic β-lactams could be active was a major departure from the previous assumption that bicyclic structures like those of the penicillins and cephalosporins were required. However, naturally occurring monobactams such as 1 and 2 (Scheme A), could not be isolated in sufficient quantities and were not readily functionalized to allow semisynthetic approaches to fully elaborate monobactam structure-activity-relationship (SAR) studies. Therefore, efforts were focused on methodology for the total syntheses of these molecules and their analogs lacking the methoxy group at the C(3) position (which is responsible for the β-lactamase stability of the natural β-lactams but also for their decreased chemical stability). Key to the syntheses of monobactams was facile construction of the N—C4 bond and most routes utilized methodology based on cyclization of β-hydroxy carboxylic acid derivatives, including hydroxamates and sulfonamides. These studies resulted in the syntheses of important antibiotics such as aztreonam (3), tigemonam (4) and carumonam (5), Scheme A. Aztreonam and carumonam display excellent antimicrobial activity, especially against Gram-negative bacteria, and are not susceptible to hydrolysis by metallo β-lactamases. However, they are only weakly active against Gram-positive bacteria.

Numerous structural modifications of these compounds have been performed in order to obtain antibiotics with improved pharmacological profiles. In particular, substitution at the C(4) position of the β-lactam ring by alkyl groups has been studied and has led to compounds with improved antibacterial activity against Gram-negative bacteria and better stability against β-lactamase enzymes. The Pfizer group reported the synthesis of monobactams with either a triazole (6, Scheme B) or an iron-chelating moiety at the C(4) position of the β-lactam ring (7). Compound 7 displayed interesting in vitro antibacterial activity against Gram-negative species including P. Aeruginosa, K. pneumonia and A. baumannii. Arnould et. al. (Eur. J. Med. Chem. 1992, 27, 131) also reported the syntheses of monocyclic β-lactams with a variety of substituted alkyl groups at the C(4) position (8). However, these compounds showed only moderate activity against Gram-negative bacteria.

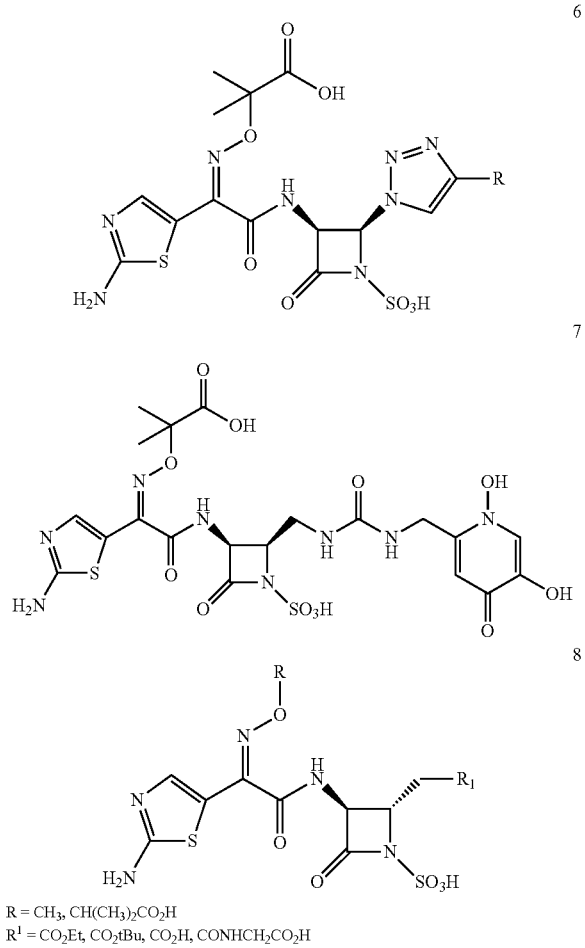

Scheme B. Synthetic C(4)-substituted monocyclic β-lactams.

R = CH₃, CH(CH₃)₂CO₂H
R¹ = CO₂Et, CO₂tBu, CO₂H, CONHCH₂CO₂H

There is an urgent need for new antibiotics, especially for pathogens of critical concern that listed by the World Health Organization (WHO). Accordingly, there is a need for antibiotics with improved antibacterial activity against drug resistant gram-negative species.

SUMMARY

A facile synthesis of 4-bromomethyl azetidinone 12 starting from commercially available vinylacetic acid (Scheme 1) was previously reported (J. Org. Chem. 1987, 52, 4471). The key step in the synthesis was the formation of the N—C4 bond of the β-lactam through a bromine-induced cyclization reaction on a γ,δ-unsaturated hydroxamate 11. The possibility of using 12 as a scaffold for further functionalization by introduction of a variety of nucleophilic groups at the C(4) position was envisaged. The syntheses and biological studies of 3-unsubstituted, 4-substituted methyl N-hydroxy β-lactams from intermediate 12 was also reported (Bioorg. Med. Chem. 2015, 23, 6138). Those studies indicated that the bromomethyl substituent in 12 could be utilized to incorporate thiols and azides. However, monobactams require an acylated amino group at C(3) of the β-lactam ring for antibiotic activity. Herein, is described the synthetic manipulation of 12 to novel 3-acylamino-N-sulfonated β-lactams with sulfur-containing functionality at the C(4) position (13, Scheme C) and subsequent antibacterial studies that extend SAR studies of monobactams.

Accordingly, this disclosure provides a compound of Formula I:

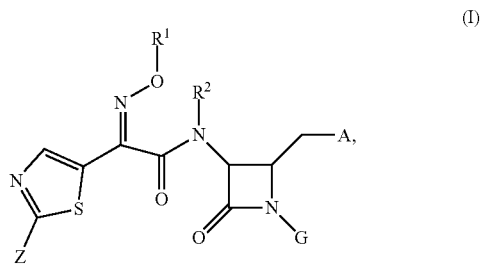

(I)

or a salt or zwitterion thereof;
wherein
A is halogen, —OR³, —SR³, or —N(R⁴)R³;
G is OR⁴, —OCHRC(=O)X, —C(=O)X, —S(=O)₂X, —OS(=O)₂X, —P(=O)X₂ or —OP(=O)X₂, wherein X is —OR^A or —N(R^A)₂;
Z is halogen, —OR⁴, —SR⁴, or —N(R⁴)₂;
R, R¹ and R² are each independently H, or —(C₁-C₁₂)alkyl;
R³ is H, —(C₁-C₁₂)alkyl, —(C₃-C₈)cycloalkyl, —(C₃-C₆)heterocycloalkyl, or —(C₁-C₈)N(R^A)R^B; and
each R^A is independently H, —(C₁-C₁₂)alkyl, —(C₃-C₈)cycloalkyl, or phenyl;
R^B is H, —(C₁-C₁₂)alkyl, —(C₃-C₈)cycloalkyl, phenyl or a moiety of Formula IB:

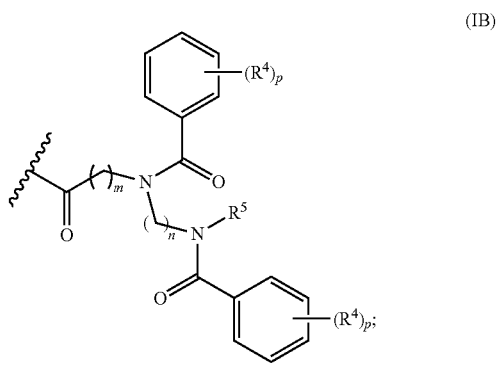

(IB)

wherein
each R⁴ is independently halogen, —(C₁-C₆)alkyl, —OR^C, —N(R^C)₂, or —C(=O)Y, wherein Y is —OR^C or —N(R^C)₂, and each R^C is independently H or —(C₁-C₁₂)alkyl.
R⁵ is H, or —(C₁-C₁₂)alkyl;

m is 1-4;

n is 1-8; and each p is independently 0-4;

wherein each —(C$_1$-C$_{12}$)alkyl and phenyl are optionally substituted with one or more substituents, and each —(C$_1$-C$_{12}$)alkyl is branched, unbranched, saturated, or unsaturated.

In some embodiments, this disclosure therefore provides gram-negative bacteria active 4-thiomethyl substituted β-lactams.

Also, this disclosure provides a pharmaceutical composition comprising a compound of Formula I and a pharmaceutically acceptable diluent, excipient, or carrier. Additionally, this disclosure provides a compound of Formula I and a second active agent wherein the second active agent is an antibiotic.

The disclosure further provides for the treatment of a bacterial infection with a β-lactams, such as a compound or composition described herein, wherein the bacterial infection is a gram-positive or a gram-negative bacterial infection.

Scheme C. Generalized structure of target molecule 13.

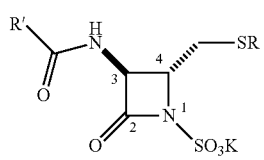

Additionally, this disclosure provides novel compounds of Formula I and Formula II, intermediates for the synthesis of compounds of Formula I and Formula II, as well as methods of preparing compounds of Formula I and II. The invention also provides compounds of Formula I and II that are useful as intermediates for the synthesis of other useful compounds. The invention provides for the use of compounds of Formula I and Formula II for the manufacture of medicaments useful for the treatment of bacterial infections in a mammal, such as a human.

The disclosure also provides for the use of the compositions described herein for use in medical therapy. The medical therapy can be treating a bacterial infection. The invention also provides for the use of a composition as described herein for the manufacture of a medicament to treat a disease in a mammal, for example, a bacterial infection in a human. The medicament can include a pharmaceutically acceptable diluent, excipient, or carrier.

Scheme 1. Synthesis of β-lactam scaffold 12.

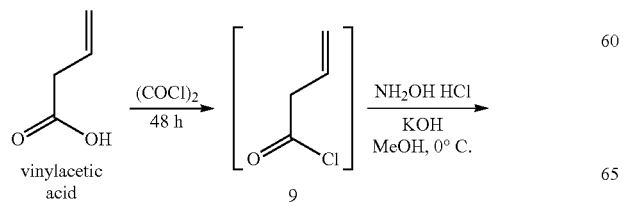

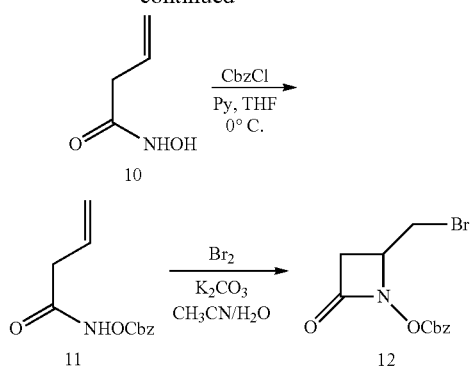

DETAILED DESCRIPTION

The retrosynthetic analysis for generalized structure 13 is displayed in Scheme 2. The target molecules, 13, with various acyl and R groups, could be obtained from 14 by a now standard sulfonation reaction. Introduction of acylamino side chains at the C(3) position would be preceded by azide reduction of compounds 15, which would be formed by direct reaction of N-tosyloxy β-lactams, 16, with azide as previously described (J. Am. Chem. Soc. 1993, 115, 548). Finally β-lactams 16 could be obtained by functional group manipulation of azetidinone 12.

Scheme 2. Retrosynthetic analysis for compounds 13.

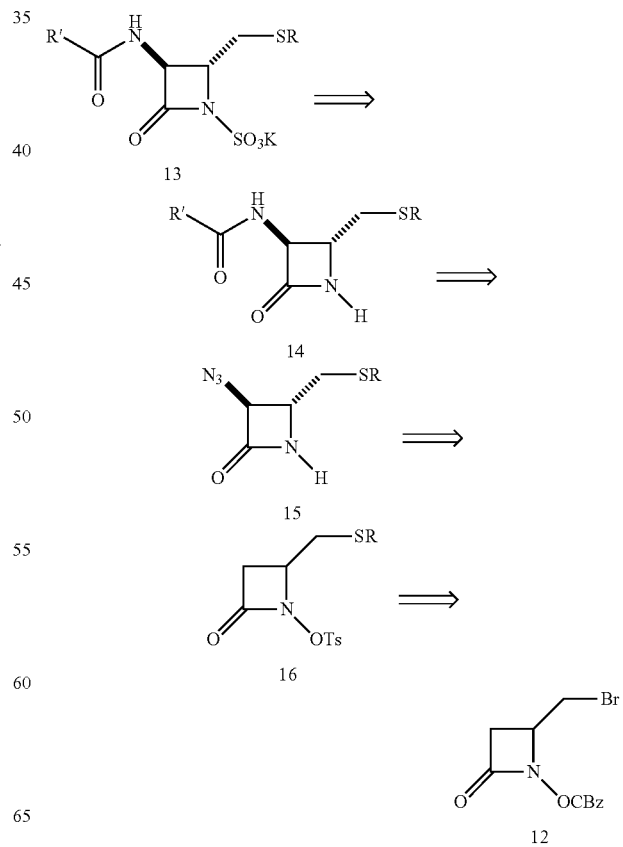

-continued

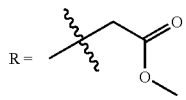

Definitions

The following definitions are included to provide a clear and consistent understanding of the specification and claims. As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14$^{th}$ Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with any element described herein, and/or the recitation of claim elements or use of "negative" limitations.

The term "and/or" means any one of the items, any combination of the items, or all of the items with which this term is associated. The phrases "one or more" and "at least one" are readily understood by one of skill in the art, particularly when read in context of its usage. For example, the phrase can mean one, two, three, four, five, six, ten, 100, or any upper limit approximately 10, 100, or 1000 times higher than a recited lower limit. For example, one or more substituents on a phenyl ring refers to one to five, or one to four, for example if the phenyl ring is disubstituted.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements. When values are expressed as approximations, by use of the antecedent "about," it will be understood that the particular value without the modifier "about" also forms a further aspect.

The terms "about" and "approximately" are used interchangeably. Both terms can refer to a variation of ±5%, ±10%, ±20%, or ±25% of the value specified. For example, "about 50" percent can in some embodiments carry a variation from 45 to 55 percent, or as otherwise defined by a particular claim. For integer ranges, the term "about" can include one or two integers greater than and/or less than a recited integer at each end of the range. Unless indicated otherwise herein, the terms "about" and "approximately" are intended to include values, e.g., weight percentages, proximate to the recited range that are equivalent in terms of the functionality of the individual ingredient, composition, or embodiment. The terms "about" and "approximately" can also modify the end-points of a recited range as discussed above in this paragraph.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. It is therefore understood that each unit between two particular units are also disclosed. For example, if 10 to 15 is disclosed, then 11, 12, 13, and 14 are also disclosed, individually, and as part of a range. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents. It will be further understood that the endpoints of each of the ranges are significant both in relation to the other endpoint, and independently of the other endpoint.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

An "effective amount" refers to an amount effective to treat a disease, disorder, and/or condition, or to bring about a recited effect. For example, an effective amount can be an amount effective to reduce the progression or severity of the condition or symptoms being treated. Determination of a therapeutically effective amount is well within the capacity of persons skilled in the art. The term "effective amount" is intended to include an amount of a compound described herein, or an amount of a combination of compounds described herein, e.g., that is effective to treat or prevent a disease or disorder, or to treat the symptoms of the disease or disorder, in a host. Thus, an "effective amount" generally means an amount that provides the desired effect.

Alternatively, the terms "effective amount" or "therapeutically effective amount," as used herein, refer to a sufficient amount of an agent or a composition or combination of compositions being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study. The dose could be administered in one or more administrations. However, the precise determination of what would be considered an effective dose may be based on factors individual to each patient, including, but not limited to, the patient's age, size, type or extent of disease, stage of the disease, route of administration of the compositions, the type or extent of supplemental therapy used, ongoing disease process and type of treatment desired (e.g., aggressive vs. conventional treatment).

The terms "treating", "treat" and "treatment" include (i) preventing a disease, pathologic or medical condition from occurring (e.g., prophylaxis); (ii) inhibiting the disease, pathologic or medical condition or arresting its development; (iii) relieving the disease, pathologic or medical condition; and/or (iv) diminishing symptoms associated with the disease, pathologic or medical condition. Thus, the terms "treat", "treatment", and "treating" can extend to prophylaxis and can include prevent, prevention, preventing, lowering, stopping or reversing the progression or severity of the condition or symptoms being treated. As such, the term "treatment" can include medical, therapeutic, and/or prophylactic administration, as appropriate.

As used herein, "subject" or "patient" means an individual having symptoms of, or at risk for, a disease or other malignancy. A patient may be human or non-human and may include, for example, animal strains or species used as "model systems" for research purposes, such a mouse model as described herein. Likewise, patient may include either adults or juveniles (e.g., children). Moreover, patient may mean any living organism, preferably a mammal (e.g., human or non-human) that may benefit from the administration of compositions contemplated herein. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the methods provided herein, the mammal is a human.

As used herein, the terms "providing", "administering," "introducing," are used interchangeably herein and refer to the placement of the compositions of the disclosure into a subject by a method or route which results in at least partial localization of the composition to a desired site. The compositions can be administered by any appropriate route which results in delivery to a desired location in the subject. The compositions described herein may be administered with additional compositions to prolong stability and activity of the compositions, or in combination with other therapeutic drugs.

The terms "inhibit", "inhibiting", and "inhibition" refer to the slowing, halting, or reversing the growth or progression of a disease, infection, condition, or group of cells. The inhibition can be greater than about 20%, 40%, 60%, 80%, 90%, 95%, or 99%, for example, compared to the growth or progression that occurs in the absence of the treatment or contacting.

The term "substantially" as used herein, is a broad term and is used in its ordinary sense, including, without limitation, being largely but not necessarily wholly that which is specified. For example, the term could refer to a numerical value that may not be 100% the full numerical value. The full numerical value may be less by about 1%, about 2%, about 3%, about 4%, about 5%, about 6%, about 7%, about 8%, about 9%, about 10%, about 15%, or about 20%.

As used herein, the term "substituted" or "substituent" is intended to indicate that one or more (for example, 1-20 in various embodiments, 1-10 in other embodiments, 1, 2, 3, 4, or 5; in some embodiments 1, 2, or 3; and in other embodiments 1 or 2) hydrogens on the group indicated in the expression using "substituted" (or "substituent") is replaced with a selection from the indicated group(s), or with a suitable group known to those of skill in the art, provided that the indicated atom's normal valency is not exceeded, and that the substitution results in a stable compound. Suitable indicated groups include, e.g., alkyl, alkenyl, alkynyl, alkoxy, halo, haloalkyl, hydroxy, hydroxyalkyl, aryl, heteroaryl, heterocycle, cycloalkyl, alkanoyl, alkoxycarbonyl, amino, alkylamino, dialkylamino, trifluoromethylthio, difluoromethyl, acylamino, nitro, trifluoromethyl, trifluoromethoxy, carboxy, carboxyalkyl, keto, thioxo, alkylthio, alkylsulfinyl, alkylsulfonyl, and cyano. Additionally, non-limiting examples of substituents that can be bonded to a substituted carbon (or other) atom include F, Cl, Br, I, OR', OC(O)N(R')$_2$, CN, CF$_3$, OCF$_3$, R', O, S, C(O), S(O), methylenedioxy, ethylenedioxy, N(R')$_2$, SR', SOR', SO$_2$R', SO$_2$N (R')$_2$, SO$_3$R', C(O)R', C(O)C(O)R', C(O)CH$_2$C(O)R', C(S) R', C(O)OR', OC(O)R', C(O)N(R')$_2$, OC(O)N(R')$_2$, C(S)N (R')$_2$, (CH$_2$)$_{0-2}$NHC(O)R', N(R')N(R')C(O)R', N(R')N(R')C (O)OR', N(R')N(R')CON(R')$_2$, N(R')SO$_2$R', N(R')SO$_2$ N(R')$_2$, N(R')C(O)OR', N(R')C(O)R', N(R')C(S)R', N(R')C (O)N(R')$_2$, N(R')C(S)N(R')$_2$, N(COR')COR', N(OR')R', C(=NH)N(R')$_2$, C(O)N(OR')R', or C(=NOR')R' wherein R' can be hydrogen or a carbon-based moiety, and wherein the carbon-based moiety can itself be further substituted. When a substituent is monovalent, such as, for example, F or Cl, it is bonded to the atom it is substituting by a single bond. When a substituent is more than monovalent, such as O, which is divalent, it can be bonded to the atom it is substituting by more than one bond, i.e., a divalent substituent is bonded by a double bond; for example, a C substituted with O forms a carbonyl group, C=O, wherein the C and the O are double bonded. Alternatively, a divalent substituent such as O, S, C(O), S(O), or S(O)$_2$ can be connected by two single bonds to two different carbon atoms. For example, O, a divalent substituent, can be bonded to each of two adjacent carbon atoms to provide an epoxide group, or the O can form a bridging ether group between adjacent or non-adjacent carbon atoms, for example bridging the 1,4-carbons of a cyclohexyl group to form a [2.2.1]-oxabicyclo system. Further, any substituent can be bonded to a carbon or other atom by a linker, such as $(CH_2)_n$ or $(CR'_2)_n$ wherein n is 1, 2, 3, or more, and each R' is independently selected.

The term "halo" or "halide" refers to fluoro, chloro, bromo, or iodo. Similarly, the term "halogen" refers to fluorine, chlorine, bromine, and iodine.

The term "alkyl" refers to a branched or unbranched hydrocarbon having, for example, from 1-20 carbon atoms, and often 1-12, 1-10, 1-8, 1-6, or 1-4 carbon atoms. As used herein, the term "alkyl" also encompasses a "cycloalkyl", defined below. Examples include, but are not limited to, methyl, ethyl, 1-propyl, 2-propyl (iso-propyl), 1-butyl, 2-methyl-1-propyl (isobutyl), 2-butyl (sec-butyl), 2-methyl-2-propyl (t-butyl), 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, hexyl, octyl, decyl, dodecyl, and the like. The alkyl can be unsubstituted or substituted, for example, with a substituent described below. The alkyl can also be optionally partially or fully unsaturated. As such, the recitation of an alkyl group can include both alkenyl and alkynyl groups. The alkyl can be a monovalent hydrocarbon radical, as described and exemplified above, or it can be a divalent hydrocarbon radical (i.e., an alkylene).

The term "cycloalkyl" refers to cyclic alkyl groups of, for example, from 3 to 10 carbon atoms having a single cyclic ring or multiple condensed rings. Cycloalkyl groups include, by way of example, single ring structures such as cyclopropyl, cyclobutyl, cyclopentyl, cyclooctyl, and the like, or multiple ring structures such as adamantyl, and the like. The cycloalkyl can be unsubstituted or substituted. The cycloalkyl group can be monovalent or divalent, and can be optionally substituted as described for alkyl groups. The cycloalkyl group can optionally include one or more cites of unsaturation, for example, the cycloalkyl group can include one or more carbon-carbon double bonds, such as, for example, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, and the like.

The term "heterocycloalkyl" refers to a saturated or partially saturated monocyclic, bicyclic, or polycyclic ring containing at least one heteroatom selected from nitrogen, sulfur, oxygen, preferably from 1 to 3 heteroatoms in at least one ring. Each ring is preferably from 3 to 10 membered, more preferably 4 to 7 membered. Examples of suitable heterocycloalkyl substituents include pyrrolidyl, tetrahydrofuryl, tetrahydrothiofuranyl, piperidyl, piperazyl, tetrahydropyranyl, morpholino, 1,3-diazapane, 1,4-diazapane, 1,4-oxazepane, and 1,4-oxathiapane. The group may be a terminal group or a bridging group.

The term "aromatic" refers to either an aryl or heteroaryl group or substituent described herein. Additionally, an aromatic moiety may be a bisaromatic moiety, a trisaromatic moiety, and so on. A bisaromatic moiety has a single bond between two aromatic moieties such as, but not limited to, biphenyl, or bipyridine. Similarly, a trisaromatic moiety has a single bond between each aromatic moiety.

The term "aryl" refers to an aromatic hydrocarbon group derived from the removal of at least one hydrogen atom from a single carbon atom of a parent aromatic ring system. The radical attachment site can be at a saturated or unsaturated carbon atom of the parent ring system. The aryl group can have from 6 to 30 carbon atoms, for example, about 6-10 carbon atoms. In other embodiments, the aryl group can have 6 to 60 carbons atoms, 6 to 120 carbon atoms, or 6 to 240 carbon atoms. The aryl group can have a single ring (e.g., phenyl) or multiple condensed (fused) rings, wherein at least one ring is aromatic (e.g., naphthyl, dihydrophenanthrenyl, fluorenyl, or anthryl). Typical aryl groups include, but are not limited to, radicals derived from benzene, naphthalene, anthracene, biphenyl, and the like. The aryl can be unsubstituted or optionally substituted.

The term "heteroaryl" refers to a monocyclic, bicyclic, or tricyclic ring system containing one, two, or three aromatic rings and containing at least one nitrogen, oxygen, or sulfur atom in an aromatic ring. The heteroaryl can be unsubstituted or substituted, for example, with one or more, and in particular one to three, substituents, as described in the definition of "substituted". Typical heteroaryl groups contain 2-20 carbon atoms in the ring skeleton in addition to the one or more heteroatoms. Examples of heteroaryl groups include, but are not limited to, 2H-pyrrolyl, 3H-indolyl, 4H-quinolizinyl, acridinyl, benzo[b]thienyl, benzothiazolyl, □-carbolinyl, carbazolyl, chromenyl, cinnolinyl, dibenzo[b,d]furanyl, furazanyl, furyl, imidazolyl, imidizolyl, indazolyl, indolisinyl, indolyl, isobenzofuranyl, isoindolyl, isoquinolyl, isothiazolyl, isoxazolyl, naphthyridinyl, oxazolyl, perimidinyl, phenanthridinyl, phenanthrolinyl, phenarsazinyl, phenazinyl, phenothiazinyl, phenoxathiinyl, phenoxazinyl, phthalazinyl, pteridinyl, purinyl, pyranyl, pyrazinyl, pyrazolyl, pyridazinyl, pyridyl, pyrimidinyl, pyrrolyl, quinazolinyl, quinolyl, quinoxalinyl, thiadiazolyl, thianthrenyl, thiazolyl, thienyl, triazolyl, tetrazolyl, and xanthenyl. In one embodiment the term "heteroaryl" denotes a monocyclic aromatic ring containing five or six ring atoms containing carbon and 1, 2, 3, or 4 heteroatoms independently selected from non-peroxide oxygen, sulfur, and N(Z) wherein Z is absent or is H, O, alkyl, aryl, or $(C_1-C_6)$alkylaryl. In some embodiments, heteroaryl denotes an ortho-fused bicyclic heterocycle of about eight to ten ring atoms derived therefrom, particularly a benz-derivative or one derived by fusing a propylene, trimethylene, or tetramethylene diradical thereto.

The term "enantiomerically enriched" ("ee") as used herein refers to mixtures that have one enantiomer present to a greater extent than another. Reactions that provide one enantiomer present to a greater extent than another would therefore be "enantioselective" (or demonstrate "enantioselectivity"). In one embodiment of the invention, the term "enantiomerically enriched" refers to a mixture having at least about 2% ee; in another embodiment of the invention, the term "enantiomerically enriched" refers to a mixture having at least about 5% ee; in another embodiment of the invention, the term "enantiomerically enriched" refers to a mixture having at least about 20%; in another embodiment of the invention, the term "enantiomerically enriched" refers to a mixture having at least about 50%; in another embodiment of the invention, the term "enantiomerically enriched" refers to a mixture having at least about 80%; in another embodiment of the invention, the term "enantiomerically enriched" refers to a mixture having at least about 90%; in another embodiment of the invention, the term "enantiomerically enriched" refers to a mixture having at least about 95%; in another embodiment of the invention, the term "enantiomerically enriched" refers to a mixture having at least about 98%; in another embodiment of the invention, the term "enantiomerically enriched" refers to a mixture having at least about 99%. The term "enantiomerically enriched" includes enantiomerically pure mixtures which are mixtures that are substantially free of the species of the opposite optical activity or one enantiomer is present in very low quantities, for example, 0.01%, 0.001% or 0.0001%.

Embodiments of the Invention

Various embodiments of the invention of compounds of Formula A and Formula B include variations at substituents $R^1$, $R^2$, $R^4$, G, Z, or X, wherein the substituents are H, alkyl, cycloalkyl, aryl, heteroaryl, halogen, or metal, and the substituents may be optionally substituted with one or more substituents of the same:

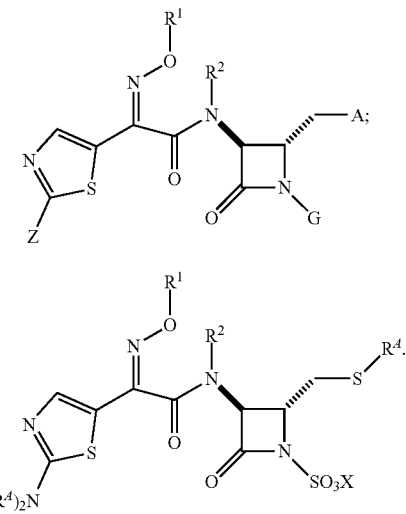

This disclosure further provides various additional embodiments of a compound of Formula I:

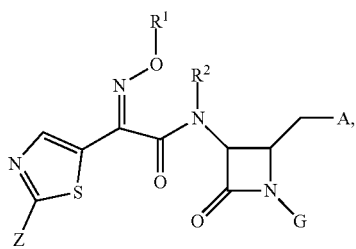

or a salt or zwitterion thereof,
wherein
A is halogen, —$OR^3$, —$SR^3$, or —$N(R^4)R^3$;
G is $OR^A$, —OCHRC(=O)X, —C(=O)X, —S(=O)$_2$X, —OS(=O)$_2$X, —P(=O)X$_2$ or —OP(=O)X$_2$, wherein X is —$OR^A$ or —$N(R^A)_2$;
Z is halogen, —$OR^A$, —$SR^A$, or —$N(R^A)_2$;
R, $R^1$ and $R^2$ are each independently H, or —($C_1$-$C_{12}$)alkyl;
$R^3$ is H, —($C_1$-$C_{12}$)alkyl, —($C_3$-$C_8$)cycloalkyl, —($C_3$-$C_6$)heterocycloalkyl, or —($C_1$-$C_8$)N($R^A$)$R^B$; and
each $R^A$ is independently H, —($C_1$-$C_{12}$)alkyl, —($C_3$-$C_8$)cycloalkyl, or phenyl;

$R^B$ is H, —($C_1$-$C_{12}$)alkyl, —($C_3$-$C_8$)cycloalkyl, phenyl or a moiety of Formula IB:

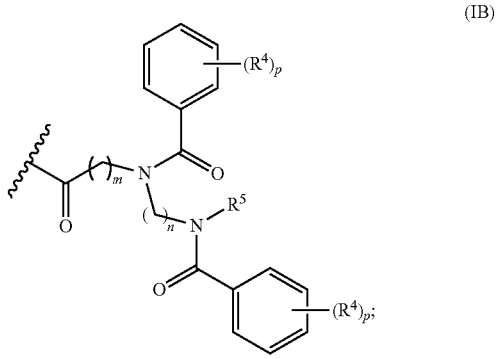

wherein
each $R^4$ is independently halogen, —($C_1$-$C_6$)alkyl, —$OR^C$, —$N(R^C)_2$, or —C(=O)Y, wherein Y is —$OR^C$ or —$N(R^C)_2$, and each $R^C$ is independently H or —($C_1$-$C_{12}$)alkyl.
$R^5$ is H, or —($C_1$-$C_{12}$)alkyl;
m is 1-4;
n is 1-8; and
each p is independently 0-4;
wherein each —($C_1$-$C_{12}$)alkyl and phenyl are optionally substituted with one or more substituents, and each —($C_1$-$C_{12}$)alkyl is branched, unbranched, saturated, or unsaturated.

In some embodiments, A is —$SR^3$ and $R^3$ is —($C_1$-$C_8$)N($R^A$)$R^B$. In other embodiments, A is —SCH$_2$CH$_2$N($R^A$)$R^B$. In additional embodiments, G is —S(=O)$_2$X and X is $OR^A$. In yet other embodiments, G is —OCHRC(=O)OH, wherein R is H or —($C_1$-$C_6$)alkyl. In some embodiments, $R^1$ is —C(CH$_3$)$_2$C(=O)OH and $R^2$ is H. In other embodiments, $R^1$ is —CH$_2$C(=O)OH. In further embodiments, Z is —$N(R^A)_2$. In some other embodiments, each $R^A$ is independently H, methyl, ethyl, propyl, cyclopropyl, allyl, vinyl, butyl, isobutyl, tert-butyl, pentyl, isopentyl, cyclopentyl, cyclohexyl, or phenyl.

In some other embodiments, $R^4$ is —$OR^A$ and p is 2. In yet other embodiments, $R^4$ is at the ortho-position, meta-position, or a combination thereof. In other embodiments, m is 1 and n is 4. In other embodiments, —($C_1$-$C_{12}$)alkyl can also be —($C_1$-$C_8$)alkyl, —($C_1$-$C_6$)alkyl, —($C_1$-$C_4$)alkyl, —($C_2$-$C_{12}$)alkyl, —($C_3$-$C_{12}$)alkyl, —($C_4$-$C_{12}$)alkyl, or —($C_5$-$C_{12}$)alkyl.

In further embodiments, the compound of Formula I is a compound of Formula II:

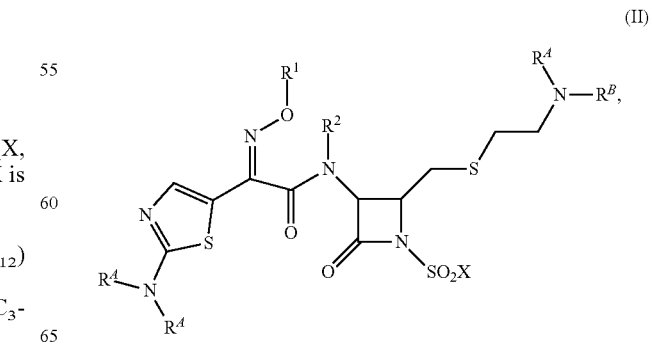

or a salt or zwitterion thereof.

In other additional embodiments, X is —OH and wherein the counterion of the salt is a metal ion, an ammonium ion, or an alkylammonium ion. In yet other embodiments, $R^A$ is H, $R^1$ is —C(CH$_3$)$_2$C(=O)OH, and $R^2$ is H.

In various additional embodiments, the stereochemistry of the carbon atom at position C3 is the (R)-configuration or the (S)-configuration. In other various embodiments, the stereochemistry of the carbon atom at position C4 is the (R)-configuration or the (S)-configuration. In yet other additional embodiments, the relative configuration of carbon atoms at positions C3 and C4 is the cis-configuration or the trans-configuration.

In some embodiments, the compound of Formula I, Formula IB or Formula II is compound 35, 39, or 42:

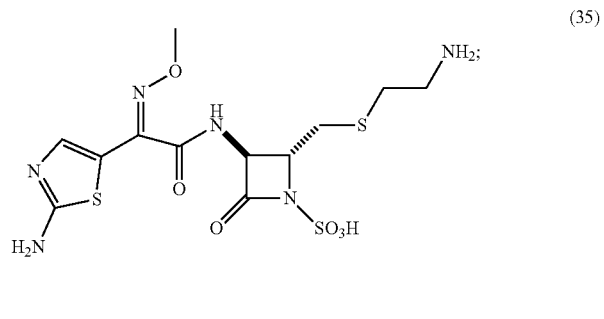
(35)

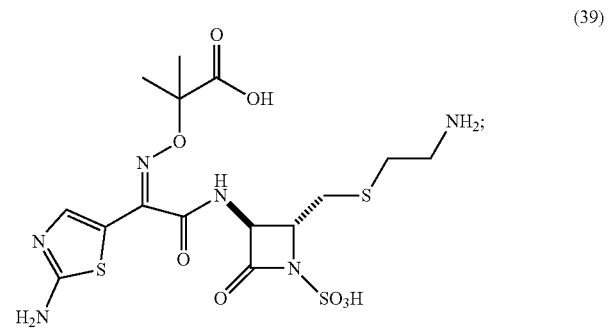
(39)

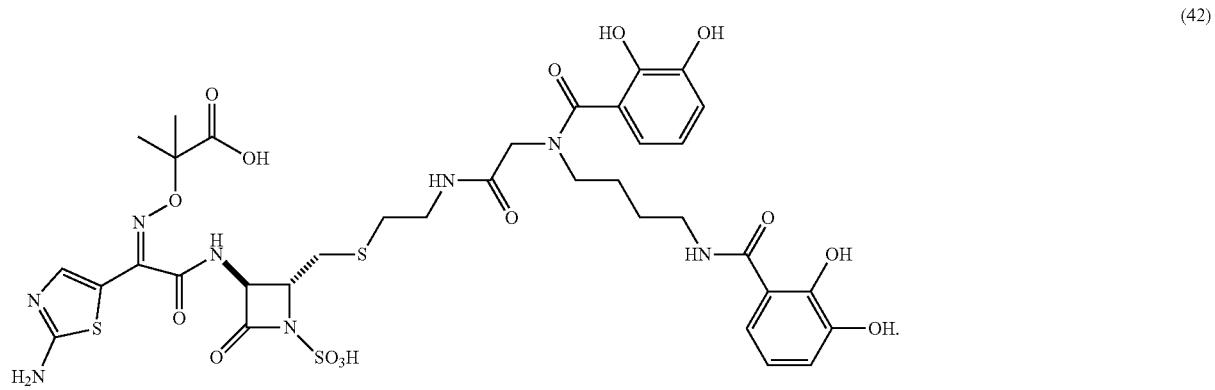
(42)

This disclosure also provides various embodiments of pharmaceutical composition comprising any compound disclosed above and a pharmaceutically acceptable diluent, excipient, or carrier. This disclosure further provides various embodiments of a compound disclosed herein and one or more second active agents. In other embodiments, the second active agent is an antibiotic. In various embodiments, the antibiotic is aztreonam, tazobactam, polymyxin, tigemonam, carumonam, or other β-lactams.

Additionally, this disclosure provides a method of treating a bacterial infection comprising administering to a subject in need thereof an effective amount of a compound disclosed herein, or a composition of a compound disclosed herein (for example, a pharmaceutical composition and an antibiotic), wherein the bacterial infection is a gram-positive or a gram-negative bacterial infection. In other embodiments, the method further comprises administering a second antibiotic to the subject.

This disclosure provides ranges, limits, and deviations to variables such as volume, mass, percentages, ratios, etc. It is understood by an ordinary person skilled in the art that a range, such as "number1" to "number2", implies a continuous range of numbers that includes the whole numbers and fractional numbers. For example, 1 to 10 means 1, 2, 3, 4, 5, . . . 9, 10. It also means 1.0, 1.1, 1.2. 1.3, . . . , 9.8, 9.9, 10.0, and also means 1.01, 1.02, 1.03, and so on. If the variable disclosed is a number less than "number10", it implies a continuous range that includes whole numbers and fractional numbers less than number10, as discussed above. Similarly, if the variable disclosed is a number greater than "number10", it implies a continuous range that includes whole numbers and fractional numbers greater than number10. These ranges can be modified by the term "about", whose meaning has been described above.

Results and Discussion

The forward synthetic direction of Scheme 2 was first tested by reaction of bromide 12 with a representative thiol, methyl thioglycolate. While the Cbz group was important for NH activation during the cyclization reaction that produced 12, it proved to be competitively electrophilic and incompatible with the intended bromide displacement by the thiol. However, hydrogenolytic removal of the Cbz group and subsequent allylation of the intermediate N-hydroxy β-lactam gave a more suitable substrate, 17, in 80% yield over two steps. Reaction of 17 with methyl thioglycolate then afforded the substitution product in high yield (Scheme 3). Similar reactions with a variety of thiols were also effective (Table 1).

Scheme 3. Syntheses of thio-substituted β-lactams 18a-f.

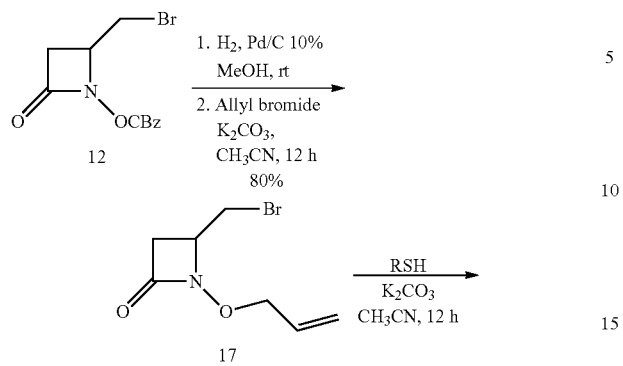

TABLE 1

Nucleophilic substitutions of β-lactam 17 with thiols.

| | RSH | Product (Yield) |
|---|---|---|
| 1 | HS—CH₂—C(O)—O—Me | 18a (70%) |
| 2 | CH₃—C(O)—SH | 18b (60%) |
| 3 | HS—C(Ph)(Ph)(Ph) | 18c (55%) |
| 4 | HS—CH₂CH₂—NHBoc | 18d (70%) |
| 5 | 2-mercaptothiazoline | 18e (71%) |
| 6 | cyclohexyl-SH | 18f (75%) |

With demonstration of the capability to incorporate thiomethyl substituents at the C4 position, methodology for incorporation of C(3) acylamino groups was first tested using a representative substrate (18a, Scheme 4). Thus, the allyl group of 18a was removed using Pd(0) chemistry and the resulting N-hydroxy β-lactam (19) was treated with TsCl under basic conditions to give N-tosyloxy β-lactam 20. Reaction of 20 with TMSN₃ and DIPEA in CH₃CN gave β-lactam 21, as a single diastereomer (racemic mixture) in which the azide group had added to the C(3) position with concomitant cleavage of the N—O bond. Although the ¹H NMR signals for CH(3) and CH(4) were not fully resolved and it was not possible to obtain their coupling constant, it was assumed initially that 21 had the trans configuration, consistent with previous results. Reduction of the azide followed by reaction of the resulting amine with phenylacetyl chloride afforded compound 22 in moderate yield. Treatment of 22 with an excess of SO₃.DMF complex gave the N-sulfonated β-lactam as the tetrabutylammonium (TBA) salt. At this point, it was possible to determine the coupling constant (J=2.8 Hz) between CH(3) and CH(4) in the ¹H NMR spectra. This result was, indeed, consistent with the trans configuration of the substituents on the β-lactam ring. Finally, ion exchange on Dowex resin (50WX8, K⁺ form) afforded the final compound 24 as the potassium salt. Again, the ¹H NMR of the final compound (24) was consistent with the trans configuration of the substituents at the C(3) and C(4) positions (J=3.0 Hz).

Scheme 4. Synthesis of N-sulfonated β-lactam 24.

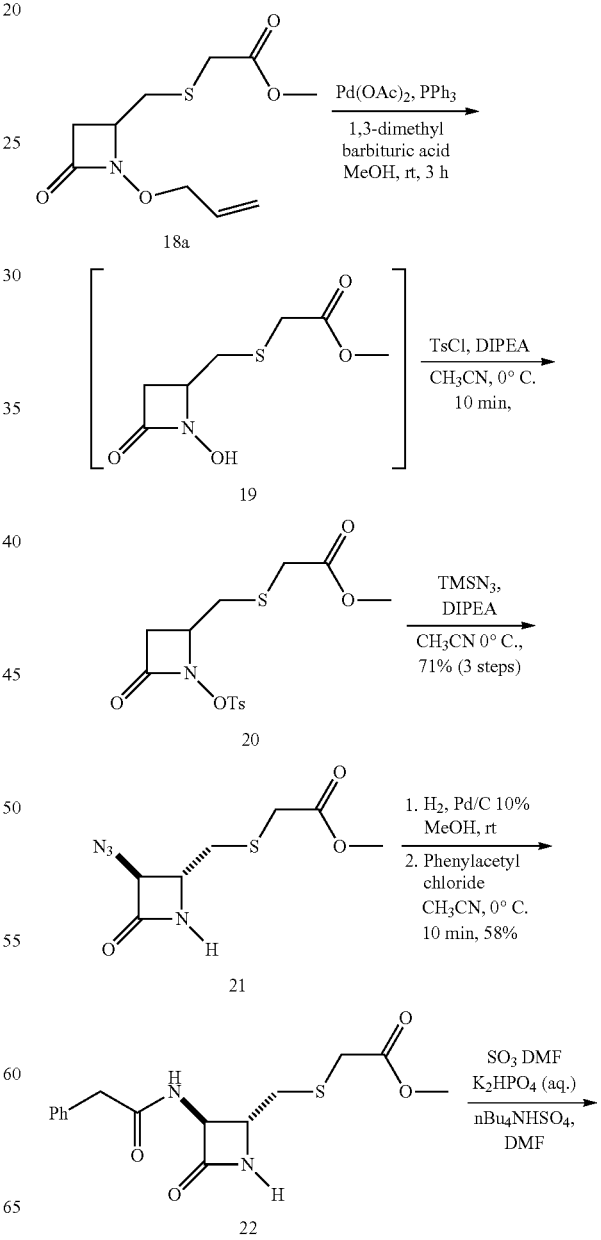

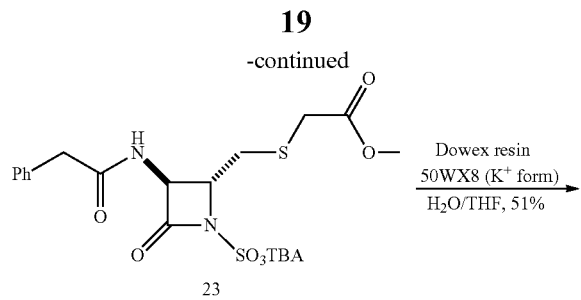

23

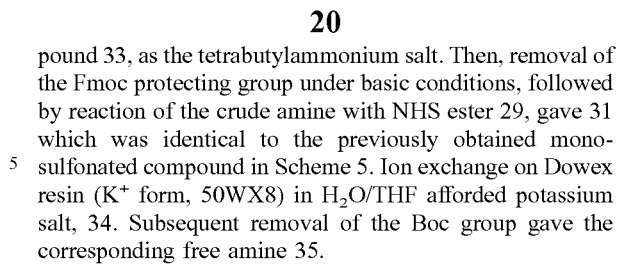

24

Although earlier monobactams with the classical penicillin G (phenylacetyl) side chain were not active antibacterial agents, β-lactam 24 was tested against a panel of Gram-negative and Gram-positive bacteria. As expected, this first derivative, made to demonstrate the overall synthetic methodology, was not active.

Having defined the synthetic route for the full elaboration of the β-lactam core 18a, the compatibility of the process with protected cysteamine derivative 18d was tested. Cysteamine derivatives are common substituents of important clinically used carbapenem antibiotics. Since compound 24 with the phenylacetamido side chain was not active, an aminothiazole methoxime (ATMO) side chain was incorporated, a simplified form of the more extended ATMO side chain of the important antibiotic aztreonam, at the C(3) position. Thus, starting from N-Boc-2-amino ethanethiol derivative, 18d, removal of the allyl protecting group was again followed by reaction of the resulting N-hydroxy β-lactam with tosyl chloride (Scheme 5). The N-tosyloxy β-lactam 26 was partially purified by column chromatography on silica gel and reacted with TMSN$_3$ under basic conditions to give the azide containing, N-unsubstituted β-lactam 27 in moderate overall yield. Again, the product was a single diastereoisomer (racemic mixture) and the coupling constant between CH(3) and CH(4) indicated the trans relationship of the substituents (J=2.0 Hz). Hydrogenolysis of the azide produced the corresponding amine (28) which was then treated with an excess of NHS ester 29 in DMF at 70° C. to give product 30, with the desired side chain. At this stage, the $^1$H NMR signals for CH(3) and CH(4) also were fully resolved and they were consistent with the trans relationship of the substituents (CH(3) doublet with J=2.3 Hz and CH(4) doublet of doublets with J=2.3, 6.3, 6.3 Hz). Finally, sulfonation of 30 with an excess of SO$_3$.DMF complex afforded the mono-sulfonated compound 31 in modest yield. All the analytical data were consistent with the structure of the mono-sulfonated compound in which the sulfonation took place on the β-lactam nitrogen and not the relatively non-nucleophilic amine substituent of the ATMO moiety. However, to confirm the sulfonation selectivity, the synthesis with an alternative route was repeated, as shown in Scheme 6.

Reduction of the azide group in 27 again gave amine 28 which reacted with FmocCl to give β-lactam 32 in moderate yield (Scheme 6). Reaction of 32 with an excess of SO$_3$.DMF complex afforded the mono-sulfonated compound 33, as the tetrabutylammonium salt. Then, removal of the Fmoc protecting group under basic conditions, followed by reaction of the crude amine with NHS ester 29, gave 31 which was identical to the previously obtained mono-sulfonated compound in Scheme 5. Ion exchange on Dowex resin (K$^+$ form, 50WX8) in H$_2$O/THF afforded potassium salt, 34. Subsequent removal of the Boc group gave the corresponding free amine 35.

Scheme 5. Synthesis of protected monobactam 31.

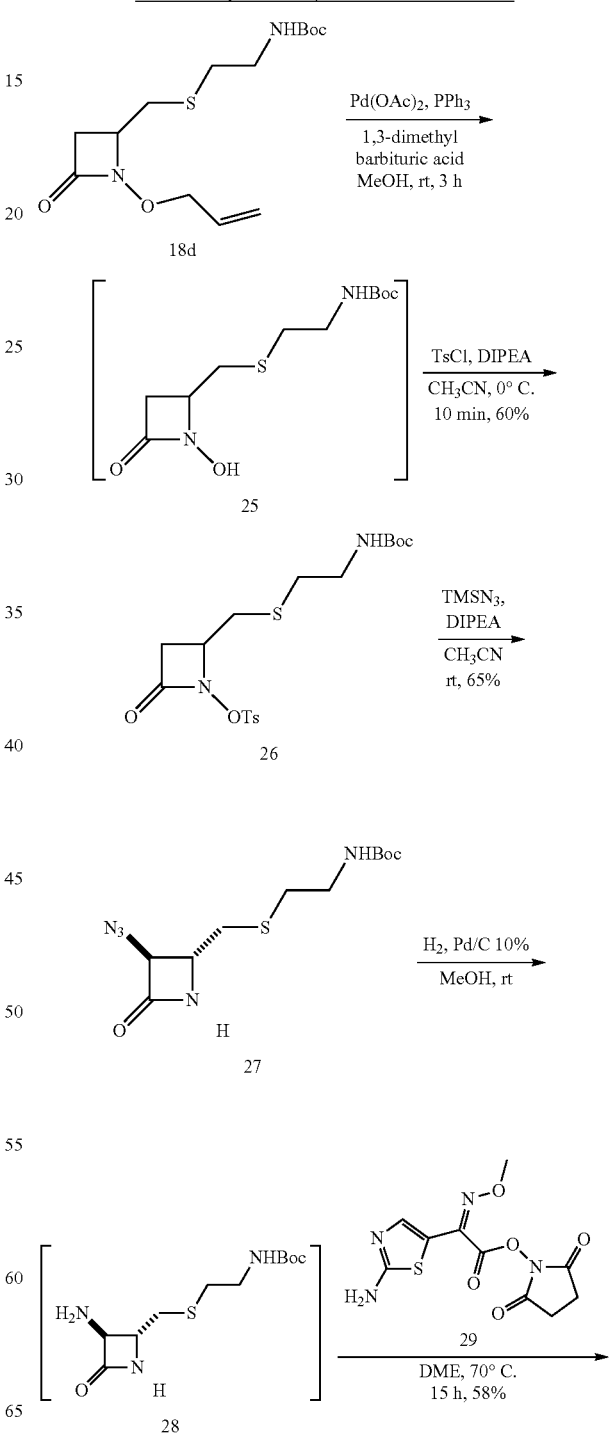

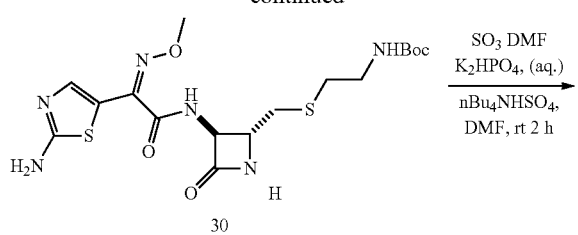

30

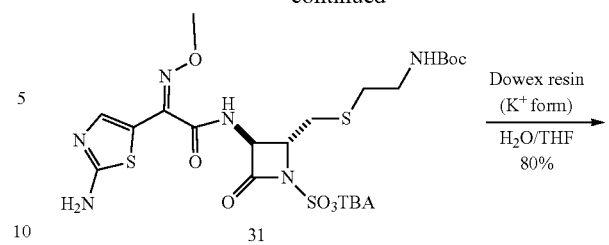

31

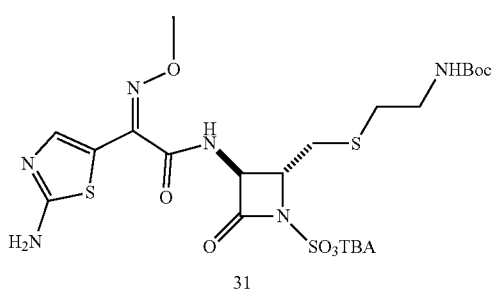

31

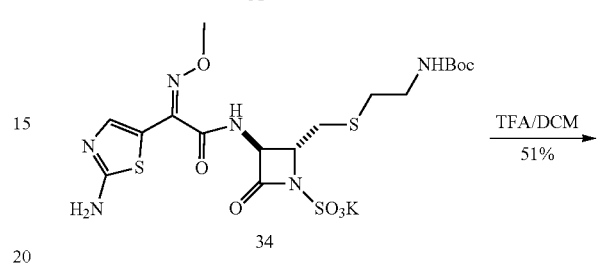

34

Scheme 6. Synthesis of final ATMO monobactam 35.

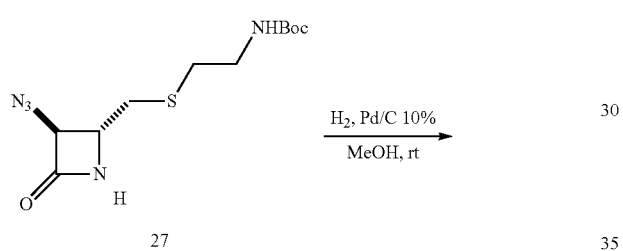

35

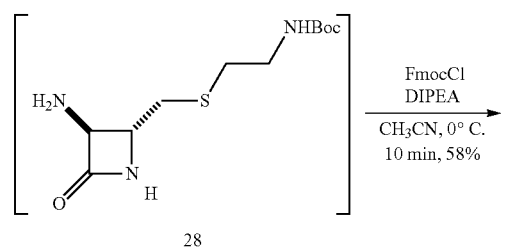

27

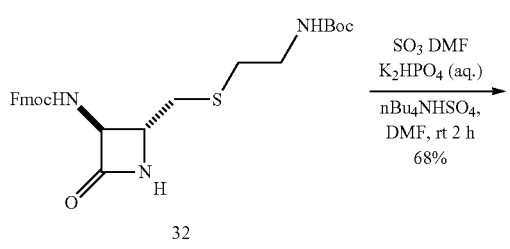

28

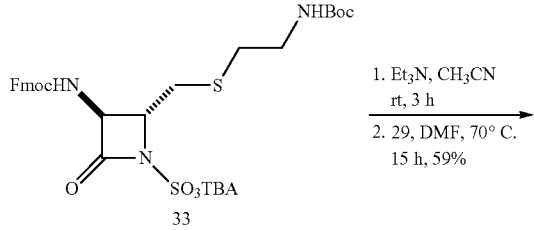

32

33

At this point the introduction of a more complex aminothiazole side chain relative to that in compound 35 was envisaged, in order to study the effect of this structural modification on the biological activity of the compound. Starting from compound 33, the same sequence of steps displayed in Scheme 6 was repeated. Again, the Fmoc group in 33 was removed under basic conditions and the resulting crude amine was reacted with NHS ester 36 in DMF at 70° C. The desired compound was purified by column chromatography on silica gel and isolated in 69% yield. At this point ion exchange was performed using Dowex resin (K$^+$ form, 50WX8) in H$_2$O/THF. The resulting potassium salt could be isolated in good yield but, although the analytical data (e.g. HPLC, HRMS, $^1$H NMR) were consistent with the structure of the desired compound, the $^1$H NMR showed the presence of an impurity which could not be removed after several attempts. Therefore it was decided to use the compound as such in the next step without further purification. Compound 38 was treated with a 1:1 mixture of DCM/TFA at rt for 1 h. After removal of the solvent and the TFA, the resulting residue was washed twice with diethyl ether and dried under vacuum. The desired compound 39 was obtained in pure form as a white solid. All the analytical data were consistent with the desired structure. In particular, the $^1$H NMR of the compound showed a coupling constant J=3.0 Hz between the CH at the C(3) and C(4) position of the β-lactam ring: this is consistent with the trans configuration of the substituents at these positions.

Scheme 7. Synthesis of free amine containing monobactam 39.

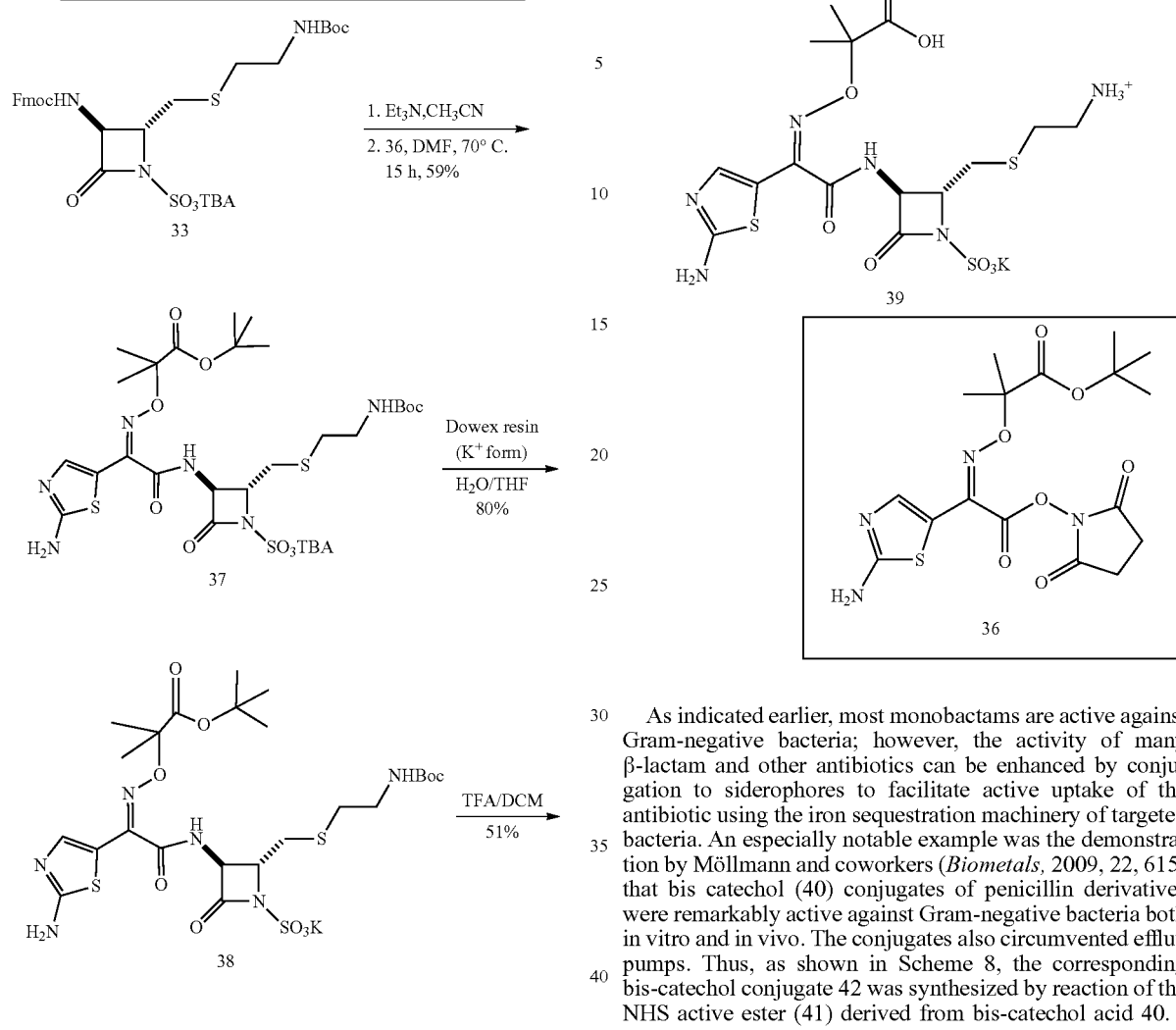

As indicated earlier, most monobactams are active against Gram-negative bacteria; however, the activity of many β-lactam and other antibiotics can be enhanced by conjugation to siderophores to facilitate active uptake of the antibiotic using the iron sequestration machinery of targeted bacteria. An especially notable example was the demonstration by Möllmann and coworkers (*Biometals,* 2009, 22, 615) that bis catechol (40) conjugates of penicillin derivatives were remarkably active against Gram-negative bacteria both in vitro and in vivo. The conjugates also circumvented efflux pumps. Thus, as shown in Scheme 8, the corresponding bis-catechol conjugate 42 was synthesized by reaction of the NHS active ester (41) derived from bis-catechol acid 40.

Scheme 8. Synthesis of siderophore-monobactam conjugate 42.

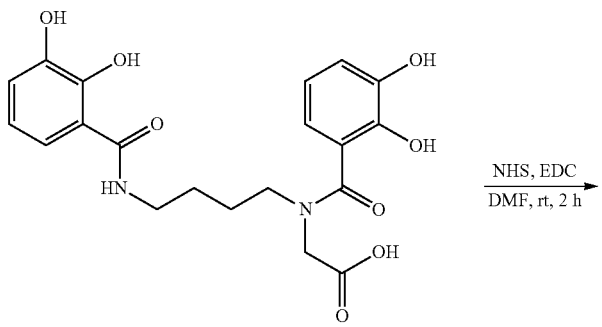

-continued
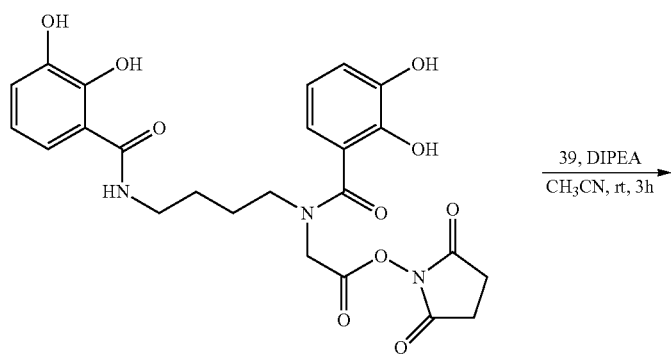
41
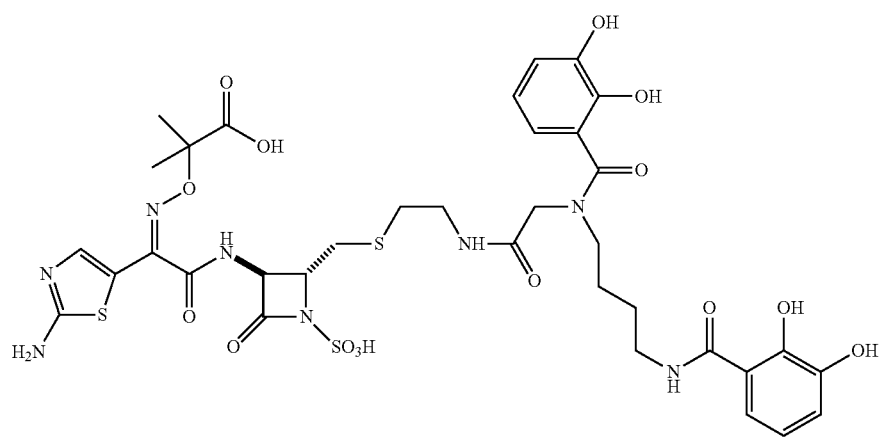
42
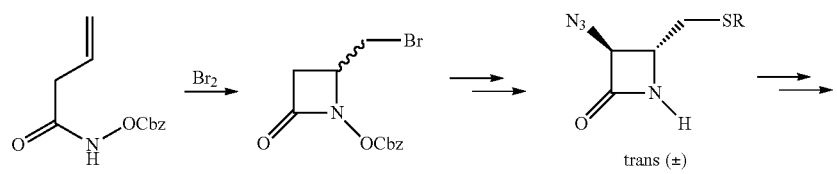
trans (±)
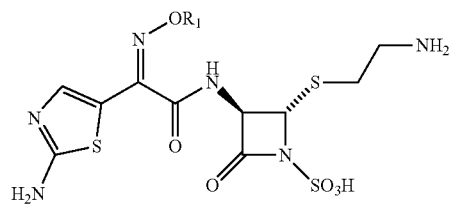

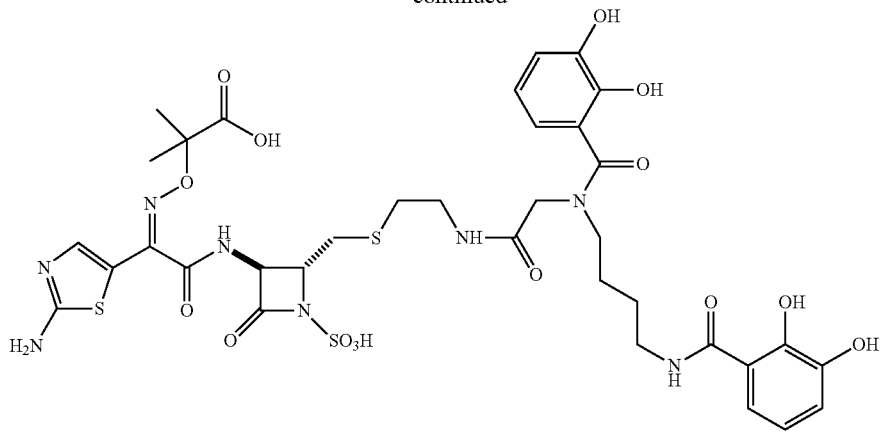

42, MIC = 0.4 µM against carbapenemase and cephalosporinase producing *Acinetobacter baumannii*

Antibacterial Assays

The final racemic sulfamates, 24, 35, 39 and conjugate 42, along with a commercial sample of aztreonam as a control, were tested for antibacterial activity. As previously stated, the 3-phenylacetamido β-lactam 24 did not show any activity (>50 µM). However, incorporation of aminothiazole side chains significantly improved activity, as expected, based on earlier studies with monobactams. As is typical for monobactams, none of the compounds were active against a representative Gram-positive strain (*Staphylococcus aureus* SG 511, Table 2). Against Gram-negative bacteria the methoxime derivative 35 was moderately active against several of the tested strains, but 39, with the same aminooxy-2-methylpropanoic acid substituent as in aztreonam had generally improved activity, though not at the same level as aztreonam itself. However, siderophore conjugate 42 was remarkably potent against several of the tested strains of Gram-negative bacteria and was generally superior to aztreonam.

None of the compounds tested were active against strong β-lactamase producing strains of *P. aeruginosa* (ARC 3502 and ARC 3506). However, studies with separate combinations of tazobactam, a β-lactamase inhibitor, revealed most improved activity from co-administration of 42 with tazobactam, whereas combination of aztreonam with tazobactam had minimal effects and 39 with tazobactam showed no improvement. Similar results were observed in studies of activity against strains of *Acinetobacter baumannii*, including clinical isolates (designated ISR in Table 2). Overall, the activity of conjugate 42 was markedly superior. Additional studies with β-lactamase producing strains of *A. baumannii* using combinations with tazobactam again showed most enhancement of activity in the combination with conjugate 42.

Polymixin, was also tested for comparison. As shown in Table 2, it has excellent activity against strains tested. Polymixins and colistin are non-ribosomal cyclic polypeptide natural products generally active against Gram-negative bacteria, but are now used only as a last resort since they are relatively neurotoxic and nephrotoxic. Resistance to polymixins/colistin is now also becoming a major concern. Most notably, conjugate 42 has outstanding activity (0.4 µM) against carbapenemase and cephalosporinase producing *A. baumannii* (ATCC 17978-PNT-165 and ATCC 17978-PNT 320, respectively).

Carbapenems are among the last resort antibiotics for treatment of many Gram-negative bacterial infections and carbapenem resistant strains of *A. baumannii*, *P. aeruginosa* and Enterobacteriaceae have recently been listed by the World Health Organization (WHO) as pathogens of critical concern. The potential of siderophore-antibiotic conjugates (ie, 42) for therapeutic use has precedent with the natural siderophore-antibiotic (sideromycin), albomycin, which was used extensively in the 1940s-1950s in the then Soviet Union. Recent reports on studies of the catechol-cephalosporin, cefiderocol, also reflect the potential of the siderophore based Trojan Horse approach to the development of useful new antibiotics.

TABLE 2

MIC values from antibacterial assays (in µM)*

| Organism | Aztreonam (+tazo) | 35 | 39 (+tazo) | 42 (+tazo) | Tazobactam (tazo) | Polymixin B |
|---|---|---|---|---|---|---|
| *S. aureus* SG 511 | >50 | >50 | >50 | >50 | | |
| *P. aeruginosa* 01 | 3 | >50 | >50 | 0.4 | | |
| *P. aeruginosa* KW799/wt | 1.6 | >50 | >50 | 0.4 | | |
| *P. aeruginosa* ARC 3502 | 50->50 | >50 | 50->50 | >50 (1.6$^a$) | >10 µg/mL | |
| *P. aeruginosa* ARC 3506 | 12.5->50 | >50 | >50 (>50) | >50 (>1.6&<25) | >10 µg/mL | |
| *P. aeruginosa* ISR-14-003$^b$ | 6 (3) | >50 | >50 | 1.6 (1.6) | >20 µg/ml | 0.1 |

TABLE 2-continued

MIC values from antibacterial assays (in μM)*

| Organism | Aztreonam (+tazo) | 35 | 39 (+tazo) | 42 (+tazo) | Tazobactam (tazo) | Polymixin B |
|---|---|---|---|---|---|---|
| P. aeruginosa ISR-14-004[b] | 50 (0.4) | >50 | >50 | 6 (3) | >20 μg/ml | 0.05 |
| E. coli DCO | 0.1 | 25 | 6 | <0.025 | | |
| Proteus mirabilis X235 | 0.05 | 12.5 | 3 | <0.025 | | |
| Salmonella typhimurium ATCC13311 | 0.1 | 12.5 | 4.5 | 0.025 | | |
| Enterobacter aerogenes X816 | 0.2 | 0.2 | 9.4 | 0.075[c] | | |
| Citrobacter freuendii ATCC 29063 | 0.1 | 12.5 | 3 | 0.05 | | |
| A. baumannii ATCC 17961 | 25 | 50 | >50 | 0.2 | | |
| A. baumannii ATCC BAA 1793 | 25-12.5 | nt | >50-50 | 0.4-0.1 | very slight inhibition @ 10 μg/ml | <0.025 |
| A. baumannii ATCC BAA 1797 | 25 | >50 | 50 | 0.4 | | |
| A. baumannii ATCC BAA 1800 | 25-12.5 | nt | 50->50 | 0.1-0.4 | very slight inhibition @ 10 μg/ml | |
| A. baumannii ISR14-005[b] | >50 (50) | >50 | >50 | >50 (25) | >20 μg/ml | <0.025 |
| A. baumannii ARC 5079 | 25-50 | nt | >50 (>50) | >1.6&<25 (>1.6&<50) | >10 μg/mL | <0.025-0.1 |
| A. baumannii ATCC17978-PNT-165[d] | 12.5 | 50 | 50 | 0.4 | | |
| A. baumannii ATCC 17978-PNT-320[e] | 50 | nt | >50 | 0.4 | <10 μg/mL | <0.025 |
| B. dolosa AU0018 | >50 | >50 | >50 | >50 | | |

*MH2 broth with 160 μM bipyridyl added.
[a] plus some growth at 50, clear between 1.6-50
[b] clinical isolate (ISR, Institute for Surgical Research)
[c] plus some slight growth in a well between
[d] carbapenemase producing organism
[e] cephalosporinase producing organism In summary, the syntheses of monocyclic β-lactams with thiomethyl and extended functionality at the C(4) position and evaluation of their activity against a panel of Gram-positive and Gram-negative bacteria are described. The results indicate that activity depends on the α-amino substituent, as is typical for monobactams. Furthermore, activity is greatly enhanced by conjugation of the newly introduced $C_4$ (p) substituents to a Gram-negative recognized bis-catechol siderophore mimic to produce new antibiotics that are remarkably active against deadly strains of carbapenemase and cephalosporinase producing A. baumannii.

Pharmaceutical Formulations

The compounds described herein can be used to prepare therapeutic pharmaceutical compositions, for example, by combining the compounds with a pharmaceutically acceptable diluent, excipient, or carrier. The compounds may be added to a carrier in the form of a salt or solvate. For example, in cases where compounds are sufficiently basic or acidic to form stable nontoxic acid or base salts, administration of the compounds as salts may be appropriate. Examples of pharmaceutically acceptable salts are organic acid addition salts formed with acids that form a physiologically acceptable anion, for example, tosylate, methanesulfonate, acetate, citrate, malonate, tartrate, succinate, benzoate, ascorbate, α-ketoglutarate, and β-glycerophosphate. Suitable inorganic salts may also be formed, including hydrochloride, halide, sulfate, nitrate, bicarbonate, and carbonate salts.

Pharmaceutically acceptable salts may be obtained using standard procedures well known in the art, for example by reacting a sufficiently basic compound such as an amine with a suitable acid to provide a physiologically acceptable ionic compound. Alkali metal (for example, sodium, potassium or lithium) or alkaline earth metal (for example, calcium) salts of carboxylic acids can also be prepared by analogous methods.

The compounds of the formulas described herein can be formulated as pharmaceutical compositions and administered to a mammalian host, such as a human patient, in a variety of forms. The forms can be specifically adapted to a chosen route of administration, e.g., oral or parenteral administration, by intravenous, intramuscular, topical or subcutaneous routes.

The compounds described herein may be systemically administered in combination with a pharmaceutically acceptable vehicle, such as an inert diluent or an assimilable edible carrier. For oral administration, compounds can be enclosed in hard or soft shell gelatin capsules, compressed into tablets, or incorporated directly into the food of a patient's diet. Compounds may also be combined with one or more excipients and used in the form of ingestible tablets, buccal tablets, troches, capsules, elixirs, suspensions, syrups, wafers, and the like. Such compositions and preparations typically contain at least 0.1% of active compound. The percentage of the compositions and preparations can vary and may conveniently be from about 0.5% to about 60%, about 1% to about 25%, or about 2% to about 10%, of the weight of a given unit dosage form. The amount of active compound in such therapeutically useful compositions can be such that an effective dosage level can be obtained.

The tablets, troches, pills, capsules, and the like may also contain one or more of the following: binders such as gum tragacanth, acacia, corn starch or gelatin; excipients such as dicalcium phosphate; a disintegrating agent such as corn starch, potato starch, alginic acid and the like; and a lubricant such as magnesium stearate. A sweetening agent such as sucrose, fructose, lactose or aspartame; or a flavoring agent such as peppermint, oil of wintergreen, or cherry flavoring, may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propyl parabens as preservatives, a dye and flavoring such as cherry or orange flavor. Any material used in preparing any unit dosage form should be pharmaceutically acceptable and substantially non-toxic in the amounts employed. In addition, the active compound may be incorporated into sustained-release preparations and devices.

The active compound may be administered intravenously or intraperitoneally by infusion or injection. Solutions of the active compound or its salts can be prepared in water, optionally mixed with a nontoxic surfactant. Dispersions can be prepared in glycerol, liquid polyethylene glycols, triacetin, or mixtures thereof, or in a pharmaceutically acceptable oil. Under ordinary conditions of storage and use, preparations may contain a preservative to prevent the growth of microorganisms.

Pharmaceutical dosage forms suitable for injection or infusion can include sterile aqueous solutions, dispersions, or sterile powders comprising the active ingredient adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions, or by the use of surfactants. The prevention of the action of microorganisms can be brought about by various antibacterial and/or antifungal agents, for example, parabens, chlorobutanol, phenol, sorbic acid, thimerosal, and the like. In many cases, it will be preferable to include isotonic agents, for example, sugars, buffers, or sodium chloride. Prolonged absorption of the injectable compositions can be brought about by agents delaying absorption, for example, aluminum monostearate and/or gelatin.

Sterile injectable solutions can be prepared by incorporating the active compound in the required amount in the appropriate solvent with various other ingredients enumerated above, as required, optionally followed by filter sterilization. In the case of sterile powders for the preparation of sterile injectable solutions, methods of preparation can include vacuum drying and freeze-drying techniques, which yield a powder of the active ingredient plus any additional desired ingredient present in the solution.

For topical administration, compounds may be applied in pure form, e.g., when they are liquids. However, it will generally be desirable to administer the active agent to the skin as a composition or formulation, for example, in combination with a dermatologically acceptable carrier, which may be a solid, a liquid, a gel, or the like.

Useful solid carriers include finely divided solids such as talc, clay, microcrystalline cellulose, silica, alumina, and the like. Useful liquid carriers include water, dimethyl sulfoxide (DMSO), alcohols, glycols, or water-alcohol/glycol blends, in which a compound can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using a pump-type or aerosol sprayer.

Thickeners such as synthetic polymers, fatty acids, fatty acid salts and esters, fatty alcohols, modified celluloses, or modified mineral materials can also be employed with liquid carriers to form spreadable pastes, gels, ointments, soaps, and the like, for application directly to the skin of the user.

Examples of dermatological compositions for delivering active agents to the skin are known to the art; for example, see U.S. Pat. No. 4,992,478 (Geria), 4,820,508 (Wortzman), 4,608,392 (Jacquet et al.), and 4,559,157 (Smith et al.). Such dermatological compositions can be used in combinations with the compounds described herein where an ingredient of such compositions can optionally be replaced by a compound described herein, or a compound described herein can be added to the composition.

Useful dosages of the compounds described herein can be determined by comparing their in vitro activity, and in vivo activity in animal models. Methods for the extrapolation of effective dosages in mice, and other animals, to humans are known to the art; for example, see U.S. Pat. No. 4,938,949 (Borch et al.). The amount of a compound, or an active salt or derivative thereof, required for use in treatment will vary not only with the particular compound or salt selected but also with the route of administration, the nature of the condition being treated, and the age and condition of the patient, and will be ultimately at the discretion of an attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound is conveniently formulated in unit dosage form; for example, containing 5 to 1000 mg, conveniently 10 to 750 mg, most conveniently, 50 to 500 mg of active ingredient per unit dosage form. In one embodiment, the invention provides a composition comprising a compound of the invention formulated in such a unit dosage form.

The compound can be conveniently administered in a unit dosage form, for example, containing 5 to 1000 mg/m$^2$, conveniently 10 to 750 mg/m$^2$, most conveniently, 50 to 500 mg/m$^2$ of active ingredient per unit dosage form. The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The compounds described herein can be effective antibacterial agents and have higher potency and/or reduced toxicity as compared to aztreonam, tazobactam, or polymyxin B. Preferably, compounds of the invention are more potent and less toxic than polymyxin B, and/or avoid a potential site of catabolic metabolism encountered with aztreonam or tazobactam, i.e., have a different metabolic profile than aztreonam or tazobactam.

The invention provides therapeutic methods of treating infections in a mammal, which involve administering to a mammal having an infection an effective amount of a compound or composition described herein. A mammal includes a primate, human, rodent, canine, feline, bovine, ovine, equine, swine, caprine, bovine and the like. An infection refers to any various type bacterial infection.

The ability of a compound of the invention to treat a bacterial infection may be determined by using assays well known to the art. For example, the design of treatment protocols, toxicity evaluation, data analysis, quantification of killing the pathogen. In addition, ability of a compound to treat a bacterial infection may be determined using the Tests as described below.

General Synthetic Methods

The invention also relates to methods of making the compounds and compositions of the invention. The compounds and compositions can be prepared by any of the applicable techniques of organic synthesis, for example, the techniques described herein. Many such techniques are well known in the art. However, many of the known techniques are elaborated in *Compendium of Organic Synthetic Methods* (John Wiley & Sons, New York), Vol. 1, Ian T. Harrison and Shuyen Harrison, 1971; Vol. 2, Ian T. Harrison and Shuyen Harrison, 1974; Vol. 3, Louis S. Hegedus and Leroy Wade, 1977; Vol. 4, Leroy G. Wade, Jr., 1980; Vol. 5, Leroy G. Wade, Jr., 1984; and Vol. 6, Michael B. Smith; as well as standard organic reference texts such as *March's Advanced Organic Chemistry: Reactions, Mechanisms, and Structure,* 5' Ed. by M. B. Smith and J. March (John Wiley & Sons, New York, 2001), *Comprehensive Organic Synthesis; Selectivity, Strategy & Efficiency in Modern Organic Chemistry*, in 9 Volumes, Barry M. Trost, Ed.-in-Chief (Pergamon Press, New York, 1993 printing)); *Advanced Organic Chemistry, Part B: Reactions and Synthesis, Second Edition,* Cary and Sundberg (1983); *Protecting Groups in Organic Synthesis, Second Edition,* Greene, T. W., and Wutz, P. G. M., John Wiley & Sons, New York; and *Comprehensive Organic Transformations*, Larock, R. C., Second Edition, John Wiley & Sons, New York (1999).

A number of exemplary methods for the preparation of the compounds of the invention are provided below. These methods are intended to illustrate the nature of such preparations are not intended to limit the scope of applicable methods.

Generally, the reaction conditions such as temperature, reaction time, solvents, work-up procedures, and the like, will be those common in the art for the particular reaction to be performed. The cited reference material, together with material cited therein, contains detailed descriptions of such conditions. Typically, the temperatures will be −100° C. to 200° C., solvents will be aprotic or protic depending on the conditions required, and reaction times will be 1 minute to 10 days. Work-up typically consists of quenching any unreacted reagents followed by partition between a water/organic layer system (extraction) and separation of the layer containing the product.

Oxidation and reduction reactions are typically carried out at temperatures near room temperature (about 20° C.), although for metal hydride reductions frequently the temperature is reduced to 0° C. to −100° C. Heating can also be used when appropriate. Solvents are typically aprotic for reductions and may be either protic or aprotic for oxidations. Reaction times are adjusted to achieve desired conversions.

Condensation reactions are typically carried out at temperatures near room temperature, although for non-equilibrating, kinetically controlled condensations reduced temperatures (0° C. to −100° C.) are also common. Solvents can be either protic (common in equilibrating reactions) or aprotic (common in kinetically controlled reactions). Standard synthetic techniques such as azeotropic removal of reaction by-products and use of anhydrous reaction conditions (e.g. inert gas environments) are common in the art and will be applied when applicable.

Protecting Groups. The term "protecting group" refers to any group which, when bound to a hydroxy or other heteroatom prevents undesired reactions from occurring at this group and which can be removed by conventional chemical or enzymatic steps to reestablish the hydroxyl group. The particular removable protecting group employed is not always critical and preferred removable hydroxyl blocking groups include conventional substituents such as, for example, allyl, benzyl, acetyl, chloroacetyl, thiobenzyl, benzylidene, phenacyl, methyl methoxy, silyl ethers (e.g., trimethylsilyl (TMS), t-butyl-diphenylsilyl (TBDPS), or t-butyldimethylsilyl (TBS)) and any other group that can be introduced chemically onto a hydroxyl functionality and later selectively removed either by chemical or enzymatic methods in mild conditions compatible with the nature of the product.

Suitable hydroxyl protecting groups are known to those skilled in the art and disclosed in more detail in T. W. Greene, *Protecting Groups In Organic Synthesis*; Wiley: New York, 1981 ("Greene") and the references cited therein, and Kocienski, Philip J.; *Protecting Groups* (Georg Thieme Verlag Stuttgart, New York, 1994), both of which are incorporated herein by reference.

Protecting groups are available, commonly known and used, and are optionally used to prevent side reactions with the protected group during synthetic procedures, i.e. routes or methods to prepare the compounds by the methods of the invention. For the most part the decision as to which groups to protect, when to do so, and the nature of the chemical protecting group "PG" will be dependent upon the chemistry of the reaction to be protected against (e.g., acidic, basic, oxidative, reductive or other conditions) and the intended direction of the synthesis.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Example 1. Experimental Methods

Abbreviations. ATMO, aminothiazole methoxime; MIC, minimum inhibitory concentration; TBA, tetra-butylammonium.

General Methods. All solvents and reagents were obtained from commercial sources and used without further purification unless otherwise stated. General methods of purification of compounds involved the use column chromatography with silica gel (230-400 mesh) purchased from Silicycle, Quebec City, Canada. The reactions were monitored by TLC on precoated Merck 60 F254 silica gel plates and visualized using UV light (254 nm). All compounds are >98% pure by HPLC analysis and MIC values reported are the average of three individual measurements.

All compounds were analyzed for purity by HPLC and characterized by $^1$H and $^{13}$C NMR using Varian 300 MHz, 500 MHz, 600 MHz NMR, and/or Bruker 400 MHz, 500 MHz NMR spectrometers. Chemical shifts are reported in ppm (δ) relative to the residual solvent peak in the corresponding spectra; chloroform 7.26 and 77.23, methanol 3.31 and 49.00 and coupling constants (J) are reported in hertz (Hz) (where, s=singlet, bs=broad singlet, d=doublet, dd=double doublet, bd=broad doublet, ddd=double doublet of dublet, t=triplet, tt—triple triplet, q=quartet, m=multiplet) and analyzed using 1D NMR processor (ACD/SpecManager) purchased from ACD labs (Product version 11.03).

The Mass spectra values are reported as m/z and HRMS analyses were carried out with a Bruker MicroOTOF-Q II, electrospray ionization time-of-flight mass spectrometer.

The liquid chromatography mass spectrum ("LC/MS") analyses were carried out on Waters ZQ instrument consisting of chromatography module Alliance HT, photodiode array detector 2996, and mass spectrometer Micromass ZQ, using a 3×50 mm Pro C18 YMC reverse phase column. Mobile phases: 10 mM ammonium acetate in HPLC grade water (A) and HPLC grade acetonitrile (B). A gradient was formed from 5% to 80% of B in 10 minutes at 0.7 mL/min. The MS electrospray source operated at capillary voltage 3.5 kV and a desolvation temperature 300° C. Reverse phase chromatographic purification was performed on a Waters 1525 Binary pump equipped with a Waters 2998 Photodiode Array Detector, Waters 2707 Autosampler, and Water Fraction Collector III utilizing Empower 3 Chromatography Manager software (Waters, Milford, Mass., USA). A Waters SymmetryPrep C18 7 μm OBD column (300×7.8 mm) was used for separation. DAD was detected at 254 nm at 20° C., eluting with a linear gradient of 0.5-20% acetonitrile in 0.1% aqueous TFA (flow rate 5 ml/min) in 30 min to afford the compound 42, retention time ($T_R$)=17 min.

Antibacterial assays were performed using iron depleted media as described previously (*J. Med. Chem.* 2017, 60, 4577).

Example 2. Synthetic Methods and Compound Characterization 1-(Allyloxy)-4-(bromomethyl)azetidin-2-one (17)

Compound 12 (4.00 g, 12.7 mmol) was dissolved in MeOH (30 mL) at rt under Argon atmosphere. Pd/C 10% (3 mmol) was added and the mixture was flushed with hydrogen gas. The reaction mixture was left to stir under an atmosphere of hydrogen, at rt, for 2.5 h then it was flushed with Argon and filtered through celite. The solvent was evaporated under vacuum to give the crude N-hydroxy β-lactam as a yellow oil. The compound was dissolved in dry CH$_3$CN (40 mL) at rt, under Argon atmosphere. K$_2$CO$_3$ (3.50 g, 25.5 mmol) was added, followed by allyl bromide (1.40 mL, 16.5 mmol). The reaction mixture was left to stir at rt for 15 h then water (20 mL) and Et$_2$O (30 mL) were added. The layers were separated and the aqueous layer was extracted with Et$_2$O (20 mL). The combined organic extracts were dried, filtered and evaporated under vacuum. Column chromatography on silica gel (hexane/EtOAc, 7:3, v/v) afforded compound 17 in 80% yield as a yellow oil (2.23 g, 10.2 mmol). IR (neat) 3082, 2955, 1777, 1644, 1420, 1343, 974. $^1$H NMR (500 MHz, CDCl$_3$) δ (ppm)=5.98 (dddd, J=6.5, 6.5, 10.3, 17.0 Hz, 1H), 5.37 (ddd, J=1.4, 2.8, 17.0 Hz, 1×CH$_2$), 5.32 (dddd, J=0.9, 0.9, 1.4, 10.3 Hz, 1×CH$_2$), 4.45 (dddd, J=1.0, 1.3, 6.5, 12.1 Hz, 1×CH$_2$), 4.41 (dddd, J=1.0, 1.3, 6.5, 12.1 Hz, 1×CH$_2$), 4.08-4.06 (m, 1H), 3.63 (dd, J=4.2, 11.0, 1×CH$_2$), 3.51 (dd, J=6.0, 11.0 Hz, 1×CH$_2$), 2.84 (dd, J=13.9, 5.4 Hz, 1×CH$_2$), 2.57 (dd, J=13.9, 2.5 Hz, 1×CH$_2$). $^{13}$C NMR (125 MHz, CDCl$_3$) δ (ppm)=164.0, 132.3, 121.3, 77.8, 57.3, 37.9, 32.1. HRMS (ESI) m/z calcd for C$_7$H$_{11}$BrNO$_2$ [M+H]+219.9973, found 219.9983.

Methyl 2-(((1-(allyloxy)-4-oxoazetidin-2-yl)methyl)thio)acetate (18a)

β-Lactam 17 (4.0 g, 18.2 mmol) was dissolved in dry CH$_3$CN (40 mL) at rt, under Argon atmosphere. K$_2$CO$_3$ (5.0 g, 36.4 mmol) was added, followed by methylthioglycolate (3.3 mL, 36.4 mmol). The resulting mixture was left to stir at rt for 15 h then it was partitioned between water (20 mL) and Et$_2$O (30 ml). The layers were separated and the aqueous layer was extracted with Et$_2$O (30 mL). The combined organic extracts were dried (Na$_2$SO$_4$), filtered and evaporated under vacuum. Column chromatography on silica gel (hexane/EtOAc, 7:3, v/v) afforded compound 18a in 70% yield, as a colorless oil (3.12 g, 12.7 mmol). $^1$H NMR (500 MHz, CDCl$_3$) δ (ppm)=6.01-5.93 (m, 1H, CH), 5.37-5.29 (m, 2H, CH$_2$), 4.44-4.38 (m, 2H, CH$_2$), 4.04-3.99 (m, 1H, CH), 3.72 (s, 3H, CH$_3$), 3.29 (d, J=14.9 Hz, 1×CH$_2$), 3.24 (d, J=14.9 Hz, 1×CH$_2$), 3.01 (dd, J=4.9, 13.8 Hz, 1×CH$_2$), 2.90 (dd, J=6.7, 13.8 Hz, 1×CH$_2$), 2.82 (dd, J=5.3, 13.8 Hz, 1×CH$_2$), 2.50 (dd, J=2.4, 13.8 Hz, 1×CH$_2$). $^{13}$C NMR (125 MHz, CDCl$_3$) δ (ppm)=170.7, 164.3, 132.4, 121.2, 77.5, 56.6, 52.8, 37.8, 34.7, 33.8. HRMS (ESI) m/z calcd for C$_{10}$H$_{16}$NO$_4$S [M+H]$^+$246.0795, found 246.0808.

1-Allyloxy-4-oxoazetidin-2-ylmethyl ethanethioate (18b)

β-Lactam 17 (300 mg, 1.36 mmol) was dissolved in 10 mL of dry CH$_3$CN at rt, under Ar atmosphere. K$_2$CO$_3$ (377 mg, 2.73 mmol) was added, followed by thioacetic acid (194 μL, 2.73 mmol). The resulting mixture was left to stir at rt for 15 h then water (10 mL) and Et$_2$O (20 ml) were added. The layers were separated and the aqueous layer was extracted with Et$_2$O (30 mL). The combined organic extracts were dried (Na$_2$SO$_4$), filtered and evaporated under vacuum. Column chromatography on silica gel (hexane/EtOAc, 4:1, v/v) afforded compound 18b in 60% yield, as a colorless oil (175 mg, 0.816 mmol). $^1$H NMR (500 MHz, CDCl$_3$) δ (ppm)=6.03-5.95 (1H, m, CH), 5.37 (1H, ddd, J=1.4, 2.7, 17.1 Hz, 1×CH$_2$), 5.35-5.32 (1H, m, 1×CH$_2$), 4.45-4.37 (2H, m, CH$_2$), 3.98-3.96 (1H, m, CH), 3.34 (1H, dd, J=4.6, 14.0 Hz, 1×CH$_2$), 3.12 (1H, dd, J=6.5, 14.0 Hz, 1×CH$_2$), 2.79 (1H, dd, J=5.4, 14.0 Hz, 1×CH$_2$), 2.40 (1H, dd, J=2.5, 14.0 Hz, 1×CH$_2$), 2.37 (3H, s, CH$_3$). $^{13}$C NMR (125 MHz, CDCl$_3$) δ (ppm)=194.8, 164.4, 132.4, 121.2, 77.5, 56.4, 37.5, 30.8, 30.7. HRMS (ESI) m/z calcd for C$_9$H$_{13}$NNaO$_3$S [M+Na]$^+$ 238.0508, found 238.0499.

1-(Allyloxy)-4-((tritylthio)methyl)azetidin-2-one (18c)

β-Lactam 17 (300 mg, 1.36 mmol) was dissolved in 10 mL of dry CH$_3$CN at rt, under Ar atmosphere. K$_2$CO$_3$ (377 mg, 2.73 mmol) was added followed by triphenylmethyl mercaptan (942 mg, 3.41 mmol). The resulting mixture was left to stir at rt for 15 h then water (10 mL) and Et$_2$O (20 ml) were added. The layers were separated and the aqueous layer was extracted with Et$_2$O (20 mL). The combined organic extracts were dried (Na$_2$SO$_4$), filtered and evaporated under vacuum. Column chromatography on silica gel (hexane/EtOAc, 4:1, v/v) afforded compound 18c in 55% yield, as a white solid (311 mg, 0.748 mmol). Mp 124-127° C.; $^1$H NMR (500 MHz, CDCl$_3$) δ (ppm)=7.46-7.42 (5H, m, CH—Ar), 7.32-7.23 (10H, m, CH—Ar), 5.90-5.84 (1H, m, CH), 5.28 (1H, d, J=12.5 Hz, CH), 5.25 (1H, d, J=5.0 Hz, CH), 4.30 (1H, dd, J=6.5, 12.0 Hz, 1×CH$_2$), 4.26 (1H, dd, J=6.5, 12.0 Hz, 1×CH$_2$), 3.48-3.46 (1H, m, CH), 2.66 (1H, dd, J=8.5, 14.0 Hz, 1×CH$_2$), 2.61 (1H, dd, J=5.5, 13.0 Hz, 1×CH$_2$), 2.43 (1H, dd, J=8.0, 13.0, 1×CH$_2$), 2.26 (1H, dd, J=2.0, 14.0 Hz, 1×CH$_2$). $^{13}$C NMR (125 MHz, CDCl$_3$) δ (ppm)=164.2, 144.6, 132.5, 129.7, 128.2, 127.3, 121.1, 77.0, 67.4, 56.3, 38.0, 34.5. HRMS (ESI) m/z calcd for C$_{26}$H$_{25}$NNaO$_2$S [M+Na]$^+$438.1498, found 438.1502.

tert-Butyl (2-(((1-(allyloxy)-4-oxoazetidin-2-yl) methyl)thio)ethyl)carbamate (18d)

Compound 17 (4.0 g, 18.2 mmol) was dissolved in dry CH$_3$CN (40 mL) at rt, under Argon atmosphere. K$_2$CO$_3$ (5.0 g, 36.4 mmol), followed by Boc cysteamine (6.4 g, 36.4 mmol). The resulting mixture was left to stir at rt for 15 h then water (20 mL) and Et$_2$O (30 ml) were added. The layers were separated and the aqueous layer was extracted with Et$_2$O (30 mL). The combined organic extracts were dried (Na$_2$SO$_4$), filtered and evaporated under vacuum. Column chromatography on silica gel (hexane/EtOAc, 1:1, v/v) afforded compound 18d as a colorless oil in 70% yield (4.0 g, 12.6 mmol). $^1$H NMR (500 MHz, CDCl$_3$) δ (ppm)=5.99-5.91 (m, 1H, CH), 5.35-5.27 (m, 2H, CH$_2$), 4.97 (bs, 1H, CH), 4.44-4.34 (m, 2H, CH$_2$), 3.98-3.94 (m, 1H, CH), 3.28-3.24 (m, 2H, CH$_2$), 2.88 (dd, J=4.7, 13.7 Hz, 1×CH$_2$), 2.78 (dd, J=5.2, 13.8 Hz, 1×CH$_2$), 2.74 (dd, J=6.8, 13.7 Hz, 1×CH$_2$), 2.69-2.60 (m, 2H, CH$_2$), 2.47 (dd, J=2.4, 13.8 Hz, 1×CH$_2$), 1.39 (s, 9H, 3×CH$_3$). $^{13}$C NMR (125 MHz, CDCl$_3$) δ (ppm)=164.3, 156.0, 132.4, 121.1, 79.7, 77.5, 57.0, 40.1, 37.8, 34.0, 33.0, 28.6. HRMS (ESI) m/z calcd for C$_{14}$H$_{25}$N$_2$O$_4$S [M+H]$^+$317.1530, found 317.1562.

1-(Allyloxy)-4-(((4,5-dihydrothiazol-2-yl)thio) methyl)azetidin-2-one (18e)

β-Lactam 17 (400 mg, 1.81 mmol) was dissolved in 10 mL of dry CH$_3$CN at rt under Ar atmosphere. K$_2$CO$_3$ (500 mg, 3.62 mmol) was added followed by 2-thiazoline-2-thiol (108 mg, 0.91 mmol). The resulting mixture was left to stir at rt for 15 h then water (10 mL) and Et$_2$O (20 ml) were added. The layers were separated and the aqueous layer was extracted with Et$_2$O (30 mL). The combined organic extracts were dried (Na$_2$SO$_4$), filtered and evaporated under vacuum. Column chromatography on silica gel (hexane/EtOAc, 4:1, v/v) afforded compound 18e in 71% yield, as a colorless oil (332 mg, 1.28 mmol). $^1$H NMR (500 MHz, CDCl$_3$) δ (ppm)=6.00 (1H, dddd, J=6.5, 6.5, 10.3, 17.1 Hz, CH), 5.38 (1H, ddd, J=1.4, 2.6, 17.1 Hz, 1×CH$_2$), 5.33 (1H, dddd, J=1.0, 1.0, 1.4, 10.3 Hz, 1×CH$_2$), 4.46-4.38 (2H, m, CH$_2$), 4.19 (2H, ddd, J=1.5, 8.0, 8.0 Hz, CH$_2$), 4.16-4.12 (1H, m, CH), 3.57 (1H, dd, J=4.9, 13.9 Hz, 1×CH$_2$), 3.42 (2H, dd, J=8.0, 8.0 Hz, CH$_2$), 3.31 (1H, dd, J=6.5, 13.9 Hz, 1×CH$_2$), 2.83 (1H, dd, J=5.3, 14.0 Hz, 1×CH$_2$), 2.54 (1H, dd, J=2.5, 14.0 Hz, 1×CH$_2$). $^{13}$C NMR (125 MHz, CDCl$_3$) δ (ppm)= 164.6, 164.5, 132.5, 121.2, 77.5, 64.2, 56.2, 37.7, 36.1, 34.0. HRMS (ESI) m/z calcd for C$_{10}$H$_{15}$N$_2$O$_2$S$_2$ [M+H]$^+$ 259.0586, found 259.0569.

1-(Allyloxy)-4-((cyclohexylthio)methyl)azetidin-2-one (18f)

β-Lactam 17 (852 mg, 3.87 mmol) was dissolved in 25 mL of dry CH$_3$CN at rt, under Ar atmosphere. K$_2$CO$_3$ (1.07 mg, 7.74 mmol) was added, followed by cyclohexane thiol (0.95 mL, 7.74 mmol). The resulting mixture was left to stir at rt for 15 h then it was partitioned between water (15 mL) and Et$_2$O (20 ml). The layers were separated and the aqueous layer was extracted with Et$_2$O (30 mL). The combined organic extracts were dried (Na$_2$SO$_4$), filtered and evaporated under vacuum. Column chromatography on silica gel (hexane/EtOAc, 4:1, v/v) afforded compound 18f in 75% yield, as a colorless oil (741 mg, 2.90 mmol). $^1$H NMR (500 MHz, CDCl$_3$) δ (ppm)=6.04-5.96 (1H, m, CH), 5.37 (1H, ddd, J=1.5, 3.0, 17.1 Hz, 5.34-5.31 (1H, m, 1×CH$_2$), 4.48-4.40 (2H, m, CH$_2$), 3.98-3.94 (1H, m, CH), 2.94 (1H, dd, J=4.5, 13.5 Hz, 1×CH$_2$), 2.93 (1H, dd, J=4.5, 13.5 Hz, 1×CH$_2$), 2.83 (1H, dd, J=5.5, 13.8 Hz, 1×CH$_2$), 2.71 (1H, dd, J=7.5, 13.5 Hz, 1×CH$_2$), 2.69-2.65 (1H, m, CH), 2.49 (1H, dd, J=2.5, 13.8 Hz, 1×CH$_2$), 1.97-1.94 (4H, m, 2×CH$_2$), 1.78-1.75 (4H, m, 2×CH$_2$), 1.63-1.60 (2H, m, CH$_2$). $^{13}$C NMR (125 MHz, CDCl$_3$) δ (ppm)=164.4, 132.5, 121.0, 77.5, 57.5, 44.5, 38.0, 33.9, 26.2, 25.9. HRMS (ESI) m/z calcd for C$_{13}$H$_{22}$NO$_2$S [M+H]$^+$256.1366, found 256.1379.

Methyl 2-(((3-azido-4-oxoazetidin-2-yl)methyl)thio) acetate (21)

PPh$_3$ (624 mg, 2.38 mmol) was added to a solution of Pd(OAc)$_2$ (133 mg, 0.59 mmol) in dry MeOH (12 mL) at rt, under Ar atmosphere and the mixture was left to stir at rt for 30 min. 1,3-Dimethylbarbituric acid (1.39 g, 8.93 mmol) was added followed by a solution of 18a (1.46 g, 5.95 mmol) in dry MeOH (10 mL). The mixture was left to stir at rt for 2 h then it was filtered through celite. The solvent was evaporated under vacuum to give crude N-hydroxy-β-lactam 19 as an orange oil. Crude compound 19 was dried under vacuum and dissolved in dry CH$_3$CN (15 mL) at rt, under Ar atmosphere. The solution was cooled to 0° C. and DIPEA (1.6 mL, 8.9 mmol) was added, followed by TsCl (1.70 mg, 8.92 mmol). The reaction mixture was left to stir at 0° C. for 10 min then the solvent was evaporated under vacuum. The residue was partially purified by column chromatography on silica gel (hexane/EtOAc, 7:3, v/v). N-Tosyloxy-β-lactam 20 was obtained as an orange oil ($^1$H NMR (500 MHz, CDCl$_3$) δ=7.87 (2H, d, J=8.0 Hz, CH—Ar), 7.37 (2H, d, J=8.0 Hz, CH—Ar), 4.23-4.19 (1H, m, CH), 3.74 (3H, s, CH$_3$), 3.28 (1H, d, J=13.5 Hz, 1×CH$_2$), 3.24 (1H, d, J=13.5 Hz, 1×CH$_2$), 3.15 (1H, dd, J=3.5, 14.5

Hz, 1×CH$_2$), 2.95-2.90 (2H, m, CH$_2$), 2.66 (1H, dd, J=3.5, 14.5 Hz, 1×CH$_2$). Compound 20 was dissolved in dry CH$_3$CN (15 mL) at rt, under Ar atmosphere. DIPEA (3.10 mL, 17.8 mmol) and TMSN$_3$ (1.57 mL, 11.9 mmol) were added sequentially. The reaction mixture was left to stir at rt for 24 h then the solvent was evaporated under vacuum. The residue was purified by column chromatography on silica gel (hexane/EtOAc, 1:1, v/v). Q-Lactam 21 was obtained as a yellow oil (347 mg, 1.51 mmol, 71% over 3 steps). $^1$H NMR (500 MHz, CDCl$_3$) δ (ppm)=6.76 (1H, bs, NH), 4.36 (1H, bs, CH), 3.75 (3H, s, CH$_3$), 3.74-3.71 (1H, m, CH), 2.98 (1H, ddd, J=1.0, 6.0, 14.0 Hz, 1×CH$_2$), 2.85 (1H, dd, J=7.0, 14.0 Hz, 1×CH$_2$). $^{13}$C NMR (125 MHz, CDCl$_3$) δ (ppm)=170.9, 164.1, 69.5, 55.8, 53.0, 35.5, 33.8. HRMS (ESI) m/z calcd for C$_7$H$_{11}$N$_4$O$_3$S [M+H]$^+$231.0546, found 231.0569.

Methyl 2-(((4-oxo-3-(2-phenylacetamido)azetidin-2-yl)methyl)thio)acetate (22)

Compound 21 (200 mg, 0.87 mmol) was dissolved in 10 mL of MeOH at rt, under Ar atmosphere. Pd/C 10% (40 mg) was added and the mixture was flushed with H$_2$. The reaction mixture was left to stir ar rt for 1.5 h then it was flushed with Ar and filtered through celite. The solvent was evaporated under vacuum to give the corresponding crude amine as a yellow oil. This was dissolved in dry CH$_3$CN (10 mL) at rt, under Ar atmosphere. The solution was cooled to 0° C. and DIPEA (227 μL, 1.30 mmol) and phenylacetyl chloride (116 μL, 0.87 mmol) were added sequentially. The mixture was left to stir at 0° C. for 10 min then the solvent was evaporated under vacuum. The residue was purified by column chromatography on silica gel (hexane/EtOAc, 4:1, v/v). Compound 22 was obtained in 58% yield (162 mg, 0.50 mmol) as a white solid. Mp 120-122° C. IR (KBr) 3318, 2959, 1786, 1736, 1648, 1521, 1453. $^1$H NMR (500 MHz, CDCl$_3$) δ (ppm)=7.37-7.25 (5H, m, CH—Ar), 6.45 (1H, NH), 6.27 (1H, bs, NH), 4.49 (1H, dd, J=2.1, 6.5 Hz, CH), 3.75-3.72 (1H, m, CH), 3.72 (3H, s, CH$_3$), 3.60 (2H, bs, CH$_2$), 3.26 (2H, bs, CH$_2$), 3.18 (1H, dd, J=4.1, 14.0 Hz, 1×CH$_2$), 2.75 (1H, dd, J=8.5, 14.0 Hz, 1×CH$_2$). $^{13}$C NMR (125 MHz, CDCl$_3$) δ (ppm)=171.9, 171.3, 166.6, 134.5, 129.6, 129.2, 127.6, 62.4, 56.6, 52.9, 43.3, 36.4, 34.2. HRMS (ESI) m/z calcd for C$_{15}$H$_{19}$N$_2$O$_4$S [M+H]$^+$323.1060, found 323.1068.

2-(((2-Methoxy-2-oxoethyl)thio)methyl)-4-oxo-3-(2-phenylacetamido)azetidine-1-sulfonate, TBA salt (23)

Compound 22 (200 mg, 0.62 mmol) was dissolved in dry DMF (10 mL) at rt, under Ar atmosphere. DMF SO$_3$ complex (475 mg, 3.10 mmol) was added and the reaction mixture was left to stir at rt for 2 h. DCM (14 mL) was added, followed by 1N K$_2$HPO$_4$ aqueous solution (5 mL). After 5 min, nBu$_4$NHSO$_4$ (210 mg, 0.62 mmol) was added. Water (6 mL) was added, the layers were separated and the aqueous layer was extracted with DCM (2×10 mL). The combined organic extracts were dried (Na$_2$SO$_4$), filtered and evaporated under vacuum. Column chromatography on silica gel (DCM/iPrOH, 4:1, v/v) gave compound 23 in 58% yield (231 mg, 0.36 mmol) as a yellow oil. $^1$H NMR (500 MHz, CDCl$_3$) δ (ppm)=7.31-7.21 (5H, m, CH—Ar), 6.71 (1H, bs, NH), 4.85 (1H, dd, J=2.8, 8.2 Hz, CH), 3.97 (1H, ddd, J=2.8, 2.8, 7.6 Hz, CH), 3.66 (3H, s, CH$_3$), 3.57 (2H, bs, CH$_2$), 3.45 (1H, d, J=15.0 Hz, 1×CH$_2$), 3.33 (1H, d, J=15.0 Hz, 1×CH$_2$), 3.29 (1H, dd, J=3.0, 14.4 Hz, 1×CH$_2$), 3.20-3.17 (8H, m, 4×CH$_2$), 3.14 (1H, dd, J=7.3, 14.4 Hz, 1×CH$_2$), 3.20-3.17 (8H, m, 4×CH$_2$), 1.61-1.55 (8H, m, 4×CH$_2$), 1.42-1.35 (8H, m, 4×CH$_2$), 0.95 (12H, dd, J=7.3, 7.3 Hz, 4×CH$_3$). $^{13}$C NMR (125 MHz, CDCl$_3$) δ (ppm) =171.3, 171.2, 163.9, 134.9, 129.7, 129.0, 127.3, 61.0, 59.3, 58.7, 52.5, 43.3, 34.5, 33.9, 24.1, 19.8, 13.9. HRMS (ESI) m/z calcd for C$_{15}$H$_{17}$N$_2$O$_7$S$_2$ [M–H]$^-$ 401.0483, found 401.0488.

Potassium 2-(((2-methoxy-2-oxoethyl)thio)methyl)-4-oxo-3-(2-phenylacetamido) azetidine-1-sulfonate (24)

Compound 23 (231 mg, 0.36 mmol) was dissolved in a 9:1 H$_2$O/THF mixture (9 mL) at rt. Dowex resin (50WX8, K$^+$ form, 60 mg) was added and the resulting mixture was left to stir at rt for 1 h. The resin was removed by filtration and new resin (60 mg) was added to the filtrate. The mixture was left to stir at rt for 1 h then the resin was removed by filtration and the solvent was evaporated under vacuum. The product was characterized without further purification (white solid, 128 mg, 0.29 mmol, 81% yield). Mp 67-70° C. $^1$H NMR (500 MHz, CDCl$_3$) δ (ppm)=7.32-7.22 (5H, m, CH—Ar), 4.55 (1H, d, J=3.0 Hz, CH), 4.15 (1H, ddd, J=3.0, 3.5, 8.5 Hz, CH), 3.61 (3H, s, CH$_3$), 3.56 (2H, s, CH$_2$), 3.28 (2H, s, CH$_2$), 3.13 (1H, dd, J=3.6, 14.4 Hz, 1×CH$_2$), 2.87 (1H, dd, J=8.9, 14.4 Hz, 1×CH$_2$). $^{13}$C NMR (125 MHz, CDCl$_3$) δ (ppm)=175.0, 173.4, 166.1, 134.7, 129.4, 129.1, 127.6, 60.0, 59.7, 53.2, 42.1, 33.7, 32.8. HRMS (ESI) m/z calcd for C$_{15}$H$_{17}$N$_2$O$_7$S$_2$ [M–H]$^-$ 401.0483, found 401.0466.

tert-Butyl (2-(((3-azido-4-oxoazetidin-2-yl)methyl) thio)ethyl)carbamate (27)

PPh$_3$ (394 mg, 1.50 mmol) was added to a solution of Pd(OAc)$_2$ (170 mg, 0.75 mmol) in dry MeOH (20 mL) at rt, under Ar atmosphere. The mixture was left to stir at rt for 30 min then 1,3-dimethylbarbituric acid (706 mg, 4.51 mmol) was added, followed by a solution of 18d (1.19 g, 3.76 mmol) in dry MeOH (20 mL). The mixture was left to stir at rt for 2 h then it was filtered through celite. The solvent was evaporated under vacuum to give crude N-hydroxy-β-lactam 25 as an orange oil. Crude compound 25 was dried under vacuum and dissolved in dry CH$_3$CN (25 mL) at rt, under Ar atmosphere. The solution was cooled to 0° C. and DIPEA (0.98 mL, 5.64 mmol) was added, followed by TsCl (1.07 mg, 5.64 mmol). The reaction mixture was left to stir at 0° C. for 10 min then the solvent was evaporated under vacuum. The residue was partially purified by column chromatography on silica gel (hexane/EtOAc, 7:3, v/v). N-Tosyloxy-β-lactam 26 was obtained as an orange oil. $^1$H NMR (500 MHz, CDCl$_3$) δ=7.89 (2H, d, J=8.5 Hz, CH—Ar), 7.39 (2H, d, J=8.5 Hz, CH—Ar), 4.20-4.16 (1H, m, CH), 3.33-3.30 (2H, m, CH$_2$), 3.05 (1H, dd, J=3.5, 14.0 Hz, 1×CH$_2$), 2.93 (1H, dd, J=6.0, 14.5 Hz, 1×CH$_2$), 2.82 (1H, dd, J=7.5, 14.0 Hz, 1×CH$_2$), 2.74-2.64 (3H, m, CH$_2$+1× CH$_2$), 2.47 (3H, s, CH$_3$), 1.45 (s, 9H, 3×CH$_3$). HRMS (ESI) m/z calcd for C$_{18}$H$_{27}$N$_2$O$_6$S$_2$ [M+H]$^+$ 431.1305, found 431.1308]. Compound 26 was dissolved in dry CH$_3$CN (20 mL) at rt, under Ar atmosphere. DIPEA (1.96 mL, 11.3 mmol) and TMSN$_3$ (0.99 mL, 7.52 mmol) were added sequentially. The reaction mixture was left to stir at rt for 24 h then the solvent was evaporated under vacuum. The residue was purified by column chromatography on silica gel (hexane/EtOAc, 1:1, v/v). Q-Lactam 27 was obtained as a yellow oil (736 mg, 2.44 mmol, 65% over 3 steps). $^1$H NMR (500 MHz, CDCl$_3$) δ (ppm)=6.82 (1H, bs, NH), 4.88 (1H, bs, NH), 4.34 (1H, dd, J=2.0, 2.0 Hz, CH), 3.69 (1H, J=2.0, 5.4, 7.2 Hz, CH), 3.30 (2H, dd, J=6.5, 13.2 Hz, CH$_2$), 2.90 (1H, dd, J=5.5, 13.9 Hz, 1×CH$_2$), 2.74 (1H, dd, J=7.3, 13.9 Hz, 1×CH$_2$), 2.68 (2H, dd, J=7.0, 7.0 Hz, CH$_2$), 1.44 (9H, s, 3×CH$_3$). $^{13}$C NMR (125 MHz, CDCl$_3$) δ (ppm) =164.4, 156.3, 80.0, 69.4, 56.3, 40.2, 34.6, 32.6, 28.6. HRMS (ESI) m/z calcd for C$_{11}$H$_{19}$N$_5$O$_3$S [M+H]$^+$302.1281, found 302.1305.

2,5-Dioxopyrrolidin-1-yl (E)-2-(2-aminothiazol-5-yl)-2-(methoxyimino)acetate (29)

(Z)-2-(2-Amino-4-thiazolyl-2-(methoxyimino)acetic acid) (2.0 g, 9.9 mmol) was dissolved in dry DMF (25 mL) at rt, under Ar atmosphere. DCC (2.26 g, 10.9 mmol) was added, followed by N-hydroxysuccinimide (1.26 g, 10.9 mmol). The mixture was left to stir at rt for 2 h then water (10 mL) was added to induce precipitation of the product. NHS ester 29 was recovered by filtration and dried under vacuum overnight (white solid, 81% yield, 8.0 mmol, 2.4 g). The compound was used without further purification. $^1$H NMR (500 MHz, DMSO) δ (ppm)=7.40 (1H, bs, CH), 3.95 (3H, s, CH$_3$), 2.87-2.85 (4H, m, 2×CH$_2$).

tert-Butyl (E)-(2-(((3-(2-(2-aminothiazol-5-yl)-2-(methoxyimino)acetamido)-4-oxoazetidin-2-yl) methyl)thio)ethyl)carbamate (30)

Compound 27 (173 mg, 0.48 mmol) was dissolved in MeOH (9 mL) at rt, under Ar atmosphere. Pd/C 10% (0.20 mmol) was added and the mixture was flushed with H$_2$. The reaction mixture was left to stir at rt for 2 h then it was flushed with Ar and filtered through celite. The solvent was evaporated under vacuum. Crude amine 28 was obtained as a yellow oil. Compound 28 was dissolved in dry DMF (5 mL) at rt, under Ar atmosphere. NHS ester 29 (266 mg, 0.72 mmol) was added and the resulting mixture was heated at 70° C. for 15 h. The mixture was left to cool to rt then the solvent was evaporated under vacuum. The resulting residue was purified by column chromatography on silica gel (DCM/iPrOH, 9:1, v/v) to give compound 30 as a yellow solid (128 mg, 0.28 mmol, 58% yield). Mp 75-78° C. $^1$H NMR (500 MHz, MeOD) δ (ppm)=6.86 (1H, s, CH), 4.69 (1H, d, J=2.3 Hz, CH), 3.96 (3H, s, CH$_3$), 3.92 (1H, ddd, J=2.3, 6.3, 6.3 Hz, CH), 3.26-3.22 (2H, m, CH$_2$), 2.94 (1H, dd, J=6.3, 13.8 Hz, 1×CH$_2$), 2.87 (1H, dd, J=6.3, 13.8 Hz, 1×CH$_2$), 2.68 (2H, dd, J=7.0, 7.0 Hz, CH$_2$), 1.43 (9H, s, 3×CH$_3$). $^{13}$C NMR (125 MHz, MeOD) δ (ppm)=170.3, 167.6, 164.1, 157.2, 148.5, 142.2, 110.9, 79.1, 62.0, 61.2, 55.7, 40.4, 34.2, 31.9, 27.6. HRMS (ESI) m/z calcd for C$_{17}$H$_{27}$N$_6$O$_5$S$_2$ [M+H]$^+$ 459.1479, found 459.1483.

(E)-3-(2-(2-Aminothiazol-5-yl)-2-(methoxyimino) acetamido)-2-(((2-((tert-butoxycarbonyl) amino) ethyl)thio)methyl)-4-oxoazetidine-1-sulfonate, TBA salt (31)

Procedure A:

Compound 30 (160 mg, 0.35 mmol) was dissolved in dry DMF (8 mL) at rt, under Ar atmosphere. SO$_3$.DMF complex (214 mg, 1.39 mmol) was added and the resulting mixture was left to stir at rt for 3 h. DCM (8 mL) was added, followed by N K$_2$HPO$_4$ aqueous solution (8 mL). nBu$_4$NHSO$_4$ (118 mg, 0.35 mmol) was added. After 10 min the layers were separated and the aqueous layer was extracted with DCM (1×10 mL). The combined organic extracts were dried (Na$_2$SO$_4$), filtered and evaporated under vacuum. The residue was purified by column chromatography on silica gel (CH$_3$CN/iPrOH, 9:1, v/v) to give compound 31 (92.2 mg, 0.17 mmol, 49% yield) as a yellow solid.

Procedure B:

Compound 33 (367 mg, 0.64 mmol) was dissolved in dry CH$_3$CN (6 mL) at rt, under Ar atmosphere. Et$_3$N (2.7 mL, 19 mmol) was added and the resulting mixture was left to stir at rt for 2 h. The solvent was evaporated under vacuum to give the crude amine as a yellow oil. Crude amine 28 was dissolved in dry DMF (10 mL) at rt, under Ar atmosphere. NHS ester 29 (474 mg, 1.28 mmol) was added and the resulting mixture was heated at 70° C. for 15 h. The solvent was evaporated under vacuum and the residue was purified by column chromatography on silica gel (CH$_3$CN/iPrOH, 9:1, v/v). Compound 31 was obtained in 59% yield (294 mg, 0.38 mmol) as a yellow solid. Mp 85-87° C. $^1$H NMR (500 MHz, MeOD) δ (ppm)=6.84 (1H, s, CH), 4.88 (1H, d, J=2.9 Hz, CH), 4.17 (1H, ddd, J=2.9, 2.9, 8.7 Hz, CH), 3.96 (3H, s, CH$_3$), 3.28-3.21 (11H, m, 1×CH$_2$+5×CH$_2$), 2.96 (1H, dd, J=8.7, 14.1 Hz, 1×CH$_2$), 2.78-2.67 (2H, m, CH$_2$), 1.68-1.62 (8H, m, 4×CH$_2$), 1.45-1.39 (8H, m, 4×CH$_2$), 1.42 (9H, s, 3×CH$_3$), 1.01 (12H, dd, J=7.3, 7.3 Hz, 4×CH$_3$). $^{13}$C NMR (125 MHz, MeOD) δ (ppm)=170.2, 163.8, 163.7, 157.1, 148.5, 142.3, 111.0, 78.9, 61.9, 60.5, 59.5, 58.3, 40.2, 32.3, 31.9, 27.6, 23.6, 19.5, 12.8. HRMS (ESI) m/z calcd for C$_{17}$H$_{25}$N$_6$O$_8$S$_3$ [M–H]$^-$ 537.0901, found 537.0931.

(9H-Fluoren-9-yl)methyl (2-(((2-((tert-butoxycarbonyl)amino)ethyl)thio)methyl)-4-oxoazetidin-3-yl) carbamate (32)

Compound 27 (500 mg, 1.38 mmol) was dissolved in 10 mL of MeOH at rt, under Ar atmosphere. Pd/C 10% (1.0 mmol) was added and the mixture was flushed with H$_2$. The reaction mixture was left to stir at rt for 2.5 h then it was flushed with Ar. The catalyst was removed by filtration and the solvent was evaporated under vacuum to give crude amine 28 as an orange oil. Crude amine 28 was dissolved in dry CH$_3$CN (10 mL) at rt, under Ar atmosphere. The solution was cooled to 0° C. and DIPEA (480 μL, 2.76 mmol) and FmocCl (714 mg, 2.76 mmol) were added sequentially. The reaction mixture was left to stir at 0° C. for 10 min then a saturated aqueous solution of citric acid (5 mL) was added. Water (10 mL) and EtOAc (20 mL) were added. The layers were separated and the aqueous layer was extracted with EtOAc (2×20 mL). The combined organic extracts were dried (Na$_2$SO$_4$), filtered and evaporated under vacuum. Column chromatography on silica gel (DCM/iPrOH, 9:1, v/v) gave product 32 as a white solid (58% yield, 398 mg, 0.80 mmol). Mp>200° C.; $^1$H NMR (500 MHz, DMSO) δ (ppm)=8.01 (1H, d, J=8.7 Hz, NH), 7.88 (2H, d, J=7.6 Hz, CH—Ar), 7.68 (2H, d, J=7.6 Hz, CH—Ar), 7.41-7.38 (2H, m, CH—Ar), 7.31 (2H, dddd, J=7.5, 7.5, 1.3, 1.3 Hz, CH—Ar), 6.90 (1H, t, J=6.0 Hz, NH), 4.36-4.29 (2H, m, CH$_2$), 4.25 (1H, dd, J=2.3, 8.7 Hz, CH), 4.21 (1H, dd, J=6.8, 6.8 Hz, CH), 3.60-3.57 (1H, m, CH), 3.08-3.04 (2H, m, CH$_2$), 2.80 (1H, dd, J=2.80 (1H, dd, J=6.8, 13.5 Hz, 1×CH$_2$), 2.69 (1H, dd, J=6.0, 13.5 Hz, 1×CH$_2$), 2.53 (2H, dd, J=7.8, 7.8 Hz, CH$_2$), 1.35 (9H, s, 3×CH$_3$). $^{13}$C NMR (125 MHz, DMSO) δ (ppm)=167.4, 156.0, 144.5, 144.4, 141.4, 128.3, 127.8, 125.8, 120.8, 78.5, 66.4, 63.2, 55.6, 47.2, 40.6, 34.7, 32.0, 28.9. HRMS (ESI) m/z calcd for C$_{26}$H$_{32}$N$_3$O$_5$S [M+H]$^+$498.2057, found 498.2080.

3-((((9H-Fluoren-9-yl)methoxy)carbonyl)amino)-2-(((2-((tert-butoxycarbonyl) amino)ethyl)thio) methyl)-4-oxoazetidine-1-sulfonate, TBA salt (33)

Compound 32 (500 mg, 1.00 mmol) was dissolved in dry DMF (20 mL) at rt, under Ar atmosphere. DMF $SO_3$ complex (923 mg, 6.00 mmol) was added and the reaction mixture was left to stir at rt for 2 h. DCM (14 mL) was added followed by 1N $K_2HPO_4$ aqueous solution (6 mL). After 5 min $nBu_4NHSO_4$ (339 mg, 1.00 mmol) was added. Water (10 mL) was added, the layers were separated and the aqueous layer was extracted with DCM (2×10 mL). The combined organic extracts were dried ($Na_2SO_4$), filtered and evaporated under vacuum. Column chromatography on silica gel ($CH_3CN$/DCM, 4:1, v/v) gave compound 33 in 68% yield (392 mg, 0.68 mmol) as a yellow solid. Mp 95-98° C. $^1H$ NMR (500 MHz, MeOD) δ (ppm)=7.78 (2H, d, J=8.0 Hz, CH—Ar), 7.64 (2H, d, J=8.0 Hz, CH—Ar), 7.38 (2H, dd, J=7.5, 7.5 Hz, CH—Ar), 7.30 (2H, dd, J=7.5, 7.5 Hz, CH—Ar), 4.63 (1H, bs, CH), 4.34 (2H, d, J=7.0 Hz, $CH_2$), 4.21 (1H, dd, J=7.0, 7.0 Hz, CH), 4.09-4.07 (1H, m, CH), 3.24-3.18 (11H, m, $1×CH_{2+5}×CH_2$), 2.95 (1H, dd, J=8.5, 14.3 Hz, $1×CH_2$), 2.75-2.63 (2H, m, $CH_2$), 1.66-1.59 (8H, m, $4×CH_2$), 1.42-1.36 (8H, m, $4×CH_2$), 1.40 (9H, s, $3×CH_3$), 0.99 (12H, dd, J=7.5, 7.5 Hz, $4×CH_3$). $^{13}C$ NMR (125 MHz, MeOD) δ (ppm)=165.5, 157.1, 156.6, 144.0, 141.4, 127.7, 127.1, 125.1, 119.8, 79.0, 67.2, 61.2, 60.9, 58.3, 47.1, 40.3, 32.4, 32.1, 27.6, 23.6, 19.5, 12.9.

Potassium (E)-3-(2-(2-aminothiazol-5-yl)-2-(methoxyimino)acetamido)-2-(((2-((tert-butoxycarbonyl)amino)ethyl)thio)methyl)-4-oxoazetidine-1-sulfonate (34)

Compound 32 (147 mg, 0.19 mmol) was dissolved in the minimum amount of THF then water was added. Dowex resin (50WX8, $K^+$ form, 60 mg) was added and the mixture was left to stir at rt for 1 h. Then the resin was removed by filtration (the resin was washed with 2 mL of water). More dowex resin (60 mg) was added to the filtrate and the mixture was left to stir at rt for 1 h. The resin was again removed by filtration and washed with water. The water was removed under high vacuum and the residue was filtered through a short pad of reverse phase silica gel ($CH_3CN$). The solvent was evaporated under vacuum to give a pale yellow solid. It was dissolved in acetone and $Et_2O$ was added causing precipitation of the product as a white solid, which was recovered by filtration and dried under vacuum (80% yield, 0.15 mmol, 87.6 mg). Mp>200° C. $^1H$ NMR (500 MHz, MeOD) δ (ppm)=6.85 (1H, s, CH), 4.79 (1H, d, J=2.9 Hz, CH), 4.22 (1H, ddd, J=2.9, 2.9, 8.8 Hz, CH), 3.28-3.22 (3H, m, $CH_2+1×CH_2$), 2.94 (1H, dd, J=8.8, 14.1 Hz, $1×CH_2$), 2.76-2.70 (2H, m, $CH_2$), 1.42 (9H, s, $3×CH_3$). $^{13}C$ NMR (125 MHz, MeOD) δ (ppm)=170.3, 164.4, 164.0, 148.3, 142.2, 110.9, 78.3, 62.0, 60.1, 59.9, 40.2, 32.3, 31.8, 27.6. HRMS (ESI) m/z calcd for $C_{17}H_{25}N_6O_8S_3$ [M−H]$^-$ 537.0901, found 537.0926.

(E)-3-(2-(2-aminothiazol-5-yl)-2-(methoxyimino)acetamido)-2-(((2-ammonioethyl) thio)methyl)-4-oxoazetidine-1-sulfonate, potassium salt (35)

Compound 34 (50 mg, 0.09 mmol) was dissolved at rt in a 4:1 DCM/TFA mixture (4 mL). The resulting mixture was left to stir at rt for 2 h then the solvent was evaporated under vacuum. Diethyl ether (3 mL) was added to induce precipitation of the product, which was recovered by filtration. Compound 36 was washed with diethyl ether twice and dried under vacuum (white solid, 20.8 mg, 0.05 mmol, 51% yield). Mp>200° C.; $^1H$ NMR (500 MHz, $D_2O$) δ (ppm) =6.98 (1H, s, CH), 4.79 (1H, d, J=2.9 Hz, CH), 4.30 (1H, ddd, J=2.9, 2.9, 7.5 Hz, CH), 3.16-3.11 (3H, m, $CH_2+1×CH_2$), 2.95 (1H, dd, J=7.8, 14.3 Hz, $1×CH_2$), 2.84 (2H, dd, J=6.7, 6.7 Hz, $CH_2$). $^{13}C$ NMR (125 MHz, $D_2O$) δ (ppm) =170.7, 164.9, 161.5, 141.7, 130.6, 111.0, 64.2, 59.9, 59.3, 38.6, 31.4, 29.1. HRMS (ESI) m/z calcd for $C_{12}H_{17}N_6O_6S_3$ [M−H]-437.0377, found 437.0356.

tert-Butyl (E)-2-(((1-(2-aminothiazol-5-yl)-2-((2,5-dioxopyrrolidin-1-yl)oxy)-2-oxoethylidene)amino)oxy)-2-methylpropanoate (36)

(Z)-2-(2-Amino-alpha-[1-(tert-butoxycarbonyl)]-1-1-methylethoxyimino-4-thiazolacetic acid (1.5 g, 4.55 mmol) was dissolved in dry DMF (25 mL) at rt, under Ar atmosphere. DCC (1.03 g, 5.00 mmol) was added, followed by N-hydroxysuccinimide (0.58 g, 5.00 mmol). The mixture was left to stir at rt for 2 h then water (10 mL) was added to induce precipitation of the product. NHS ester 36 was recovered by filtration and dried under vacuum overnight (white solid, 75% yield, 3.41 mmol, 1.45 g). The compound was used without further purification.

(E)-3-(2-(2-aminothiazol-5-yl)-2-(((1-(tert-butoxy)-2-methyl-1-oxopropan-2-yl)oxy)imino)acetamido)-2-(((2-((tert-butoxycarbonyl)amino)ethyl)thio)methyl)-4-oxoazetidine-1-sulfonate, TBA salt (37)

Compound 33 (238 mg, 0.46 mmol) was dissolved in dry $CH_3CN$ at rt under Ar atmosphere. $Et_3N$ (642 µL, 4.6 mmol) was added and the reaction mixture was left to stir at rt for 2 h. The solvent was evaporated under vacuum and the resulting residue (the crude amine) was dried under vacuum. It was dissolved in dry DMF (5 mL) at rt and NHS ester 36 (353 mg, 0.83 mmol) was added. The mixture was heated at 70° C. for 15 h then it was left to cool to rt. The solvent was evaporated under vacuum and the residue was purified by column chromatography on silica gel ($CH_3CN$/DCM, 7:3, v/v). Compound 37 (210 mg, 0.31 mmol, 69% yield) was obtained as a yellow solid. Mp 68-70° C. $^1H$ NMR (500 MHz, $CDCl_3$) δ (ppm)=7.80 (1H, bs, NH), 6.99 (2H, bs, $NH_2$), 6.82 (s, 1H, CH), 5.20 (1H, bs, NH), 4.89 (1H, dd, J=2.3, 8.3 Hz, CH), 4.18-4.16 (1H, m, CH), 3.30-3.21 (m, 11H, $CH_2+1×CH_2+4×CH_2$), 3.03 (1H, dd, J=7.5, 14.5 Hz, $1×CH_2$), 2.82-2.79 (1H, m, $1×CH_2$), 2.70-2.63 (1H, m, $1×CH_2$), 1.64-1.58 (8H, m, $4×CH_2$), 1.54 (3H, s, $CH_3$), 1.52 (3H, s, $CH_3$), 1.43-1.38 (26H, m, $4×CH_2+3×CH_{3+3}×CH_3$), 0.96 (12H, dd, J=7.4, 7.4 Hz, $4×CH_3$). $^{13}C$ NMR (125 MHz, $CDCl_3$) δ (ppm)=174.0, 170.0, 163.7, 162.5, 156.1, 149.4, 142.4, 110.1, 83.1, 82.5, 79.3, 60.8, 59.2, 58.7, 40.1, 32.6, 28.6, 28.2, 24.3, 24.1, 23.7, 19.8, 13.9. HRMS (ESI) m/z calcd for $C_{24}H_{37}N_6O_{10}S_3$ [M−H]-665.1739, found 665.1736.

Potassium (E)-3-(2-(2-aminothiazol-5-yl)-2-(((1-(tert-butoxy)-2-methyl-1-oxopropan-2-yl)oxy)imino)acetamido)-2-(((2-((tert-butoxycarbonyl)amino)ethyl) thio)methyl)-4-oxoazetidine-1-sulfonate (38)

Compound 37 (147 mg, 0.22 mmol) was dissolved in the minimum amount of THF then water was added. Dowex resin (50WX8, K+ form, 60 mg) was added and the mixture was left to stir at rt for 1 h. Then the resin was removed by filtration (the resin was washed with 2 mL of water). More dowex resin (60 mg) was added to the filtrate and the mixture was left to stir at rt for 1 h. The resin was again removed by filtration and washed with water. The water was removed under high vacuum and the residue was purified by column chromatography on silica gel (from DCM/CH$_3$CN 1:1 to CH$_3$CN to CH$_3$CN/2-propanol, 9:1, v/v) to give the product (81% yield, 0.18 mmol, 119 mg) as a yellow solid. It was dissolved in acetone and Et$_2$O was added causing precipitation of the product 38 as a white solid, which was recovered by filtration and dried under vacuum (80% yield, 0.15 mmol, 87.6 mg). $^1$H NMR (500 MHz, CDCl$_3$) δ (ppm)=4.87 (1H, d, J=3.0 Hz, CH), 4.24 (1H, dt, J=3.0, 8.5 Hz, 1×CH$_2$), 3.28-3.22 (3H, m, CH$_2$+1×CH$_2$), 3.00 (1H, dd, J=8.5, 14.3 Hz, 1×CH$_2$), 2.79-2.73 (1H, m, 1×CH$_2$), 2.71-2.66 (1H, m, 1×CH$_2$). HRMS (ESI) m/z calcd for C$_{24}$H$_{37}$N$_6$O$_{10}$S$_3$ [M−H]$^-$ 665.1739, found 665.1714.

(E)-3-(2-(2-aminothiazol-5-yl)-2-(((2-carboxypropan-2-yl)oxy)imino)acetamido)-2-(((2-ammonioethyl)thio)methyl)-4-oxoazetidine-1-sulfonate, potassium salt (39)

Compound 38 (50 mg, 0.08 mmol) was dissolved at rt in a 4:1 DCM/TFA mixture (4 mL). The resulting mixture was left to stir at rt for 2 h then the solvent was evaporated under vacuum. Diethyl ether (3 mL) was added to induce precipitation of the product, which was recovered by filtration. Compound 39 was washed with diethyl ether twice and dried under vacuum (white solid, 19.5 mg, 0.04 mmol, 51% yield). $^1$H NMR (500 MHz, D$_2$O) δ (ppm)=7.02 (1H, s, CH), 4.86 (1H, d, J=3.0 Hz, CH), 4.31 (1H, ddd, J=3.0, 3.0, 8.0 Hz, CH), 3.19-3.15 (3H, m, 1×CH$_2$+CH$_2$), 2.98 (1H, dd, J=8.0, 14.0 Hz, 1×CH$_2$), 2.88 (1H, dd, J=7.0 Hz, 1×CH$_2$), 1.48 (s, 6H, 2×CH$_3$). $^{13}$C NMR (125 MHz, D$_2$O) δ (ppm) =178.3, 170.9, 164.7, 161.8, 143.3, 131.2, 111.8, 84.8, 60.1, 59.5, 38.5, 31.5, 29.2, 23.4. HRMS (ESI) m/z calcd for C$_{15}$H$_{21}$N$_6$O$_8$S$_3$ [M−H]$^-$ 509.0588, found 509.0561.

(E)-2-(((1-(2-Aminothiazol-5-yl)-2-((2-(8-(2,3-dihydroxybenzoyl)-14-(2,3-dihydroxyphenyl)-6,14-dioxo-2-thia-5,8,13-triazatetradecyl)-4-oxo-1-sulfoazetidin-3-yl)amino)-2-oxoethylidene)amino)oxy)-2-methylpropanoic acid (42)

To a solution of compound 40 (0.12 mmol, 51 mg) and NHS (0.14 mmol, 17 mg) in dry DMF (5 mL) at room temperature, was added EDC.HCl (0.15 mmol, 29 mg). The mixture was stirred for 2 h at room temperature to give a NHS active ester (41) solution, which was used directly in the following coupling reaction. To a suspension of 39 (0.1 mmol, 55 mg) in dry acetonitrile (5 mL), was added DIPEA (0.2 mmol, 35 µL) at room temperature. To this mixture was added the NHS active ester (41) DMF solution. Then the mixture was stirred at room temperature for 3 h and monitored by LC-MS. When the reaction was finished, the solvent was evaporated under reduced pressure, and the residue was purified by Prep-HPLC to give the final compound 42 as a white solid in 21% yield. $^1$H NMR (500 MHz, DMSO-d$_6$) δ (ppm)=1.16 (d, J=10 Hz, 1H), 1.29-1.35 (m, 2H), 1.42 (s, 6H), 1.57 (brs, 2H), 2.59-2.74 (m, 2H), 2.83-2.88 (m, 1H), 3.09-3.18 (m, 5H), 3.28-3.40 (m, 2H), 3.58-3.76 (m, 2H), 3.84-3.92 (m, 2H), 4.05 (s, 1H), 4.71 (s, 1H), 6.52-6.78 (m, 6H), 6.88 (d, J=10 Hz, 1H), 7.23-7.34 (m, 3H), 7.95-8.01 (m, 1H), 8.71-8.84 (m, 2H), 10.20-10.47 (m, 1H). $^{13}$C NMR (600 MHz, DMSO-d$_6$) δ (ppm)=24.21, 24.37, 25.30, 25.66, 26.08, 30.62, 31.94, 38.33, 38.60, 44.74, 47.46, 48.38, 50.98, 51.37, 58.79, 59.30, 82.56, 109.78, 114.99, 115.74, 117.09, 117.32, 117.54, 118.51, 119.43, 124.95, 141.52, 143.04, 145.49, 146.10, 149.66, 149.83, 162.57, 168.19, 169.30, 169.52, 177.57. HRMS (ESI) m/z calcd for C$_{35}$H$_{42}$N$_8$NaO$_{15}$S$_3$ [M+Na]$^+$ 933.1835, found 933.1824.

Example 3. Pharmaceutical Dosage Forms

The following formulations illustrate representative pharmaceutical dosage forms that may be used for the therapeutic or prophylactic administration of a compound of a formula described herein, a compound specifically disclosed herein, or a pharmaceutically acceptable salt or solvate thereof (hereinafter referred to as 'Compound X'):

| (i) Tablet 1 | mg/tablet |
| --- | --- |
| 'Compound X' | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
| --- | --- |
| 'Compound X' | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
| --- | --- |
| 'Compound X' | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/mL) | mg/mL |
| --- | --- |
| 'Compound X' (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/mL) | mg/mL |
| --- | --- |
| 'Compound X' (free acid form) | 10.0 |
| Monobasic sodium phosphate | 0.3 |
| Dibasic sodium phosphate | 1.1 |

| (v) Injection 2 (10 mg/mL) | mg/mL |
|---|---|
| Polyethylene glycol 400 | 200.0 |
| 0.1N Sodium hydroxide solution (pH adjustment to 7.0-7.5) | q.s. |
| Water for injection | q.s. ad 1 mL |

| (vi) Aerosol | mg/can |
|---|---|
| 'Compound X' | 20 |
| Oleic acid | 10 |
| Trichloromonofluoromethane | 5,000 |
| Dichlorodifluoromethane | 10,000 |
| Dichlorotetrafluoroethane | 5,000 |

| (vii) Topical Gel 1 | wt. % |
|---|---|
| 'Compound X' | 5% |
| Carbomer 934 | 1.25% |
| Triethanolamine (pH adjustment to 5-7) | q.s. |
| Methyl paraben | 0.2% |
| Purified water | q.s. to 100 g |

| (viii) Topical Gel 2 | wt. % |
|---|---|
| 'Compound X' | 5% |
| Methylcellulose | 2% |
| Methyl paraben | 0.2% |
| Propyl paraben | 0.02% |
| Purified water | q.s. to 100 g |

| (ix) Topical Ointment | wt. % |
|---|---|
| 'Compound X' | 5% |
| Propylene glycol | 1% |
| Anhydrous ointment base | 40% |
| Polysorbate 80 | 2% |
| Methyl paraben | 0.2% |
| Purified water | q.s. to 100 g |

| (x) Topical Cream 1 | wt. % |
|---|---|
| 'Compound X' | 5% |
| White bees wax | 10% |
| Liquid paraffin | 30% |
| Benzyl alcohol | 5% |
| Purified water | q.s. to 100 g |

| (xi) Topical Cream 2 | wt. % |
|---|---|
| 'Compound X' | 5% |
| Stearic acid | 10% |
| Glyceryl monostearate | 3% |
| Polyoxyethylene stearyl ether | 3% |

| (xi) Topical Cream 2 | wt. % |
|---|---|
| Sorbitol | 5% |
| Isopropyl palmitate | 2% |
| Methyl Paraben | 0.2% |
| Purified water | q.s. to 100 g |

These formulations may be prepared by conventional procedures well known in the pharmaceutical art. It will be appreciated that the above pharmaceutical compositions may be varied according to well-known pharmaceutical techniques to accommodate differing amounts and types of active ingredient 'Compound X'. Aerosol formulation (vi) may be used in conjunction with a standard, metered dose aerosol dispenser. Additionally, the specific ingredients and proportions are for illustrative purposes. Ingredients may be exchanged for suitable equivalents and proportions may be varied, according to the desired properties of the dosage form of interest.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

What is claimed is:

1. A compound of Formula I:

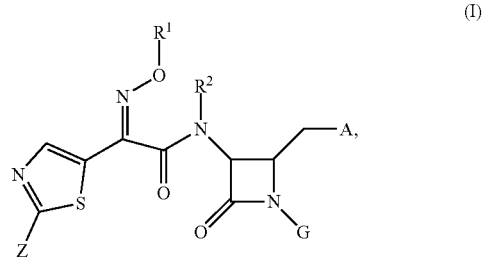

or a salt or zwitterion thereof;
wherein
A is halogen, —$OR^3$, —$SR^3$, or —$N(R^4)R^3$;
G is $OR^A$, —$OCHRC(=O)X$, —$C(=O)X$, —$S(=O)_2X$, —$OS(=O)_2X$, —$P(=O)X_2$ or —$OP(=O)X_2$, wherein X is —$OR^A$ or —$N(R^A)_2$;
Z is halogen, —$OR^A$, —$SR^A$, or —$N(R^A)_2$;
R, $R^1$ and $R^2$ are each independently H, or —$(C_1$-$C_{12})$alkyl;
$R^3$ is —$(C_1$-$C_8)N(R^A)R^B$; and
each $R^A$ is independently H, —$(C_1$-$C_{12})$alkyl, —$(C_3$-$C_8)$cycloalkyl, or phenyl;

$R^B$ is Formula IB:

(IB)

[Structure of Formula IB showing wavy bond to carbonyl, (CH2)m, N, C=O connected to phenyl with (R4)p, and (CH2)n-N(R5)-C(=O)-phenyl with (R4)p]

wherein
each $R^4$ is independently halogen, —($C_1$-$C_6$)alkyl, —$OR^C$, —$N(R^C)_2$, or —C(=O)Y,
wherein Y is —$OR^C$ or —$N(R^C)_2$, and each $R^C$ is independently H or —($C_1$-$C_{12}$)alkyl;
$R^5$ is H, or —($C_1$-$C_{12}$)alkyl;
m is 1-4;
n is 1-8; and
each p is independently 0-4;
wherein each —($C_1$-$C_{12}$)alkyl and phenyl are optionally substituted with one or more substituents, and each —($C_1$-$C_{12}$)alkyl is branched, unbranched, saturated, or unsaturated.

2. The compound of claim 1 wherein A is —$SR^3$ and $R^3$ is —($C_1$-$C_8$)N($R^A$)$R^B$.

3. The compound of claim 1 wherein A is —$SCH_2CH_2N(R^A)R^B$.

4. The compound of claim 1 wherein G is —S(=O)2X and X is $OR^A$.

5. A compound of Formula I:

(I)

[Structure of Formula I: thiazole with Z substituent, connected via C=N-OR1 to C(=O)-N(R2)- attached to a β-lactam ring with CH2-A substituent and N-G]

or a salt or zwitterion thereof;
wherein
A is halogen, —$OR^3$, —$SR^3$, or —$N(R^4)R^3$;
G is —OCHRC(=O)OH, wherein R is H or —($C_1$-$C_6$)alkyl;
Z is halogen, —$OR^A$, —$SR^A$, or —$N(R^A)_2$;
R, $R^1$ and $R^2$ are each independently H, or —($C_1$-$C_{12}$)alkyl;
$R^3$ is H, —($C_1$-$C_{12}$)alkyl, —($C_3$-$C_8$)cycloalkyl, —($C_3$-$C_6$)heterocycloalkyl, or —($C_1$-$C_8$)N($R^A$)$R^B$; and
each $R^A$ is independently H, —($C_1$-$C_{12}$)alkyl, —($C_3$-$C_8$)cycloalkyl, or phenyl;
$R^B$ is H, —($C_1$-$C_{12}$)alkyl, —($C_3$-$C_8$)cycloalkyl, phenyl or a moiety of Formula IB:

(IB)

[Structure of Formula IB showing wavy bond to C=O, (CH2)m, N connected to two C(=O)-phenyl groups each bearing (R4)p, with N-R5]

wherein
each $R^4$ is independently halogen, —($C_1$-$C_6$)alkyl, —$OR^C$, —$N(R^C)_2$, or —C(=O)Y, wherein Y is —$OR^C$ or —$N(R^C)_2$ and each $R^C$ is independently H or —$C_1$-$C_{12}$ alkyl;
$R^5$ is H, or —($C_1$-$C_{12}$)alkyl;
m is 1-4;
n is 1-8; and
each p is independently 0-4;
wherein each —($C_1$-$C_{12}$)alkyl and phenyl are optionally substituted with one or more substituents, and each —($C_1$-$C_{12}$)alkyl is branched, unbranched, saturated, or unsaturated.

6. The compound of claim 1 wherein $R^1$ is —$C(CH_3)_2$C(=O)OH and $R^2$ is H.

7. The compound of claim 1 wherein Z is —$N(R^A)_2$.

8. The compound of claim 1 wherein each $R^A$ is independently H, methyl, ethyl, propyl, cyclopropyl, allyl, vinyl, butyl, isobutyl, tert-butyl, pentyl, isopentyl, cyclopentyl, cyclohexyl, or phenyl.

9. The compound of claim 1 wherein $R^4$ is —$OR^A$ and p is 2.

10. The compound of claim 1 wherein m is 1 and n is 4.

11. A compound of Formula II:

(II)

[Structure of Formula II: thiazole with $R^A$-N-$R^A$ amino group, connected via C=N-OR1 to C(=O)-N(R2)- attached to β-lactam with CH2-S-CH2CH2-N($R^A$)$R^B$ and N-SO2X]

or a salt or zwitterion thereof;
wherein
$R^1$ and $R^2$ are each independently H, or —($C_1$-$C_{12}$)alkyl;
each $R^A$ is independently H, —($C_1$-$C_{12}$)alkyl, —($C_3$-$C_8$)cycloalkyl, or phenyl; and $R^B$ is Formula IB:

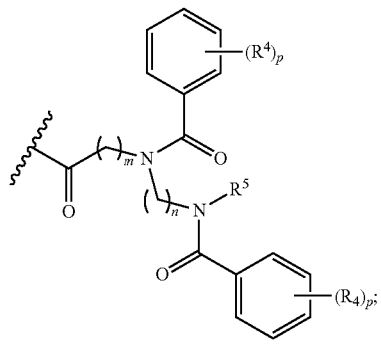

wherein
each $R^4$ is independently halogen, —$(C_1$-$C_6)$alkyl, —$OR^C$, —$N(R^C)_2$, or —$C(=O)Y$, wherein Y is —$OR^C$ or —$N(R^C)_2$ and each $R^C$ is independently H or —$C_1$-$C_{12}$ alkyl;
$R^5$ is H, or —$(C_1$-$C_{12})$alkyl;
m is 1-4;
n is 1-8; and
each p is independently 0-4;
wherein each —$(C_1$-$C_{12})$alkyl and phenyl are optionally substituted with one or more substituents, and each —$(C_1$-$C_{12})$alkyl is branched, unbranched, saturated, or unsaturated.

12. The compound of claim 11 wherein X is —OH and wherein the counterion of the salt is a metal ion, an ammonium ion, or an alkylammonium ion.

13. The compound of claim 11 wherein $R^4$ is H, $R^1$ is —$C(CH_3)_2C(=O)OH$, and $R^2$ is H.

14. The compound of claim 11 wherein the stereochemistry of the carbon atom at position C3 or C4 is the (R)-configuration.

15. The compound of claim 11 wherein the stereochemistry of the carbon atom at position C3 or C4 is the (S)-configuration.

16. The compound of claim 11 wherein the relative configuration of carbon atoms at positions C3 and C4 is the trans-configuration.

17. The compound of claim 11 wherein the compound is 42:

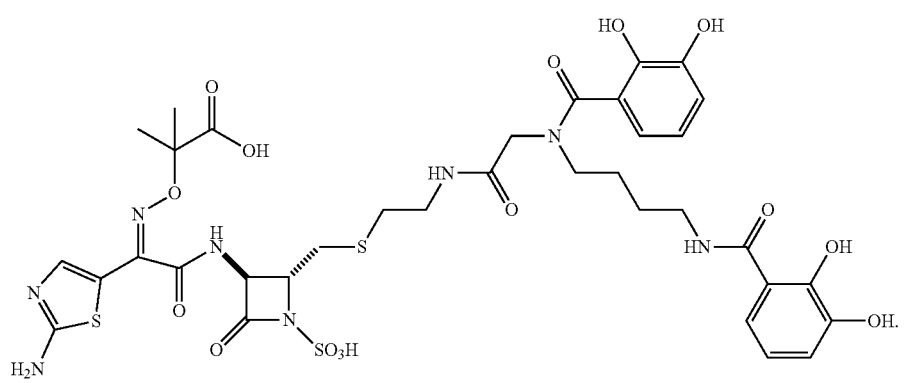

18. A pharmaceutical composition comprising a compound of claim 1 and a pharmaceutically acceptable diluent, excipient, or carrier.

19. A composition comprising a compound of claim 1 and a second active agent wherein the second active agent is an antibiotic.

20. The composition of claim 19 wherein the antibiotic is aztreonam, tazobactam, or polymixin.

21. A method of treating a bacterial infection comprising administering to a subject in need thereof an effective amount of a compound of claim 1 wherein the bacterial infection is thereby treated.

* * * * *